US011981755B2

(12) United States Patent
Öberg et al.

(10) Patent No.: US 11,981,755 B2
(45) Date of Patent: May 14, 2024

(54) PEPTIDE COMPOUNDS

(71) Applicant: ULTUPHARMA AB, Uppsala (SE)

(72) Inventors: Bo Öberg, Uppsala (SE); Anders Broberg, Uppsala (SE); Bengt Guss, Uppsala (SE); Jolanta Levenfors, Örbyhus (SE); Joakim Bjerketorp, Uppsala (SE); Christina Nord, Uppsala (SE)

(73) Assignee: ULTUPHARMA AB, Uppsala (SE)

( * ) Notice: Subject to any disclaimer, the term of this patent is extended or adjusted under 35 U.S.C. 154(b) by 0 days.

(21) Appl. No.: 17/268,694

(22) PCT Filed: Aug. 27, 2019

(86) PCT No.: PCT/SE2019/050789
§ 371 (c)(1),
(2) Date: Feb. 16, 2021

(87) PCT Pub. No.: WO2020/046190
PCT Pub. Date: Mar. 5, 2020

(65) Prior Publication Data
US 2021/0269483 A1 Sep. 2, 2021

(30) Foreign Application Priority Data

Aug. 28, 2018 (SE) .................................. 1851022-2
Jul. 10, 2019 (SE) .................................. 1950877-9

(51) Int. Cl.
*A61K 38/00* (2006.01)
*C07K 7/56* (2006.01)
*C12P 21/02* (2006.01)

(52) U.S. Cl.
CPC ................ *C07K 7/56* (2013.01); *C12P 21/02* (2013.01); *A61K 38/00* (2013.01)

(58) Field of Classification Search
None
See application file for complete search history.

(56) References Cited

U.S. PATENT DOCUMENTS 5,830,855 A    11/1998    Takemoto

FOREIGN PATENT DOCUMENTS

EP    2708551 A1    3/2014
JP    2005 200324 A    7/2005

OTHER PUBLICATIONS

Barreto, Glossary: Infections diseases epidemiology, J Epidemical Community, 2006:60; 192-195. (Year: 2006).*
Kim, Jueum et al, "Isolation and structural elucidation of pelgipeptin E, a novel poreforming pelgipeptin analog from Paenibacillus elgii with low hemolytic activity", The Journal of Antibiotics, (2018) 71: 1008-1017.
Shiho Kozuma et al: "Screening and biological activities of pedopeptins, novel inhibitors of LPS produced by soil bacteria", The Journal of Antibiotics, (2014), 67, 237-242.
Yuki Hirota-Takahata et al, "Pedopeptidns, novel inhibitors of LPS: Taxonomy of producing organism, fermentation, isolation, physicochemical properties and structural elucidation", The Journal of Antibiotics, (2014), 67, 243-251.
Swedish Search Report issued in SWE 1851022-2 dated Aug. 28, 2018, 2 pages.
International Search Report issued in PCT/SE2019/050789 dated Feb. 4, 2020, 3 pages.

* cited by examiner

*Primary Examiner* — Thomas S Heard
(74) *Attorney, Agent, or Firm* — Rothwell, Figg, Ernst & Manbeck, P.C.

(57) ABSTRACT

The present invention relates to novel compounds, which presents a peptide structure and an unexpected antibacterial effect even against certain multiresistant bacteria. The compounds may be cyclic peptides, sometimes depsipeptides, or non-ring-closed peptides, as defined by Formula (I). Further, the invention relates to the medical use of the herein claimed compounds, a method for the production of the compounds as well as a method of treatment including the compounds. In addition, the invention relates to a pharmaceutical preparation comprising one or more of the herein described and claimed compounds combined with suitable carrier(s) and/or adjuvant(s). Finally, the invention is the use of one or more of the claimed compounds in a method for decolonization of a surface of Gram-positive and/or Gram-negative bacteria.

23 Claims, 5 Drawing Sheets
Specification includes a Sequence Listing.

SEQUENCE LISTING

```
<160> NUMBER OF SEQ ID NOS: 5

<210> SEQ ID NO 1
<211> LENGTH: 10
<212> TYPE: PRT
<213> ORGANISM: Pedobacter sp. UP508
<220> FEATURE:
<221> NAME/KEY: MISC_FEATURE
<222> LOCATION: (1)..(1)
<223> OTHER INFORMATION: 3-hydroxydecanoyl
<220> FEATURE:
<221> NAME/KEY: MISC_FEATURE
<222> LOCATION: (2)..(2)
<223> OTHER INFORMATION: DAPA
<220> FEATURE:
<221> NAME/KEY: MISC_FEATURE
<222> LOCATION: (4)..(4)
<223> OTHER INFORMATION: DABA
<220> FEATURE:
<221> NAME/KEY: MISC_FEATURE
<222> LOCATION: (5)..(5)
<223> OTHER INFORMATION: ABA
<220> FEATURE:
<221> NAME/KEY: MISC_FEATURE
<222> LOCATION: (7)..(7)
<223> OTHER INFORMATION: DAPA
<220> FEATURE:
<221> NAME/KEY: MISC_FEATURE
<222> LOCATION: (9)..(9)
<223> OTHER INFORMATION: OHVal

<400> SEQUENCE: 1

Xaa Xaa Leu Xaa Xaa Thr Xaa Phe Val Asp
1               5                   10

<210> SEQ ID NO 2
```

```
<211> LENGTH: 10
<212> TYPE: PRT
<213> ORGANISM: Pedobactersp.UP508
<220> FEATURE:
<221> NAME/KEY: MISC_FEATURE
<222> LOCATION: (1)..(1)
<223> OTHER INFORMATION: 3-hydroxy-11-methyldodecanoyl
<220> FEATURE:
<221> NAME/KEY: MISC_FEATURE
<222> LOCATION: (2)..(2)
<223> OTHER INFORMATION: DAPA
<220> FEATURE:
<221> NAME/KEY: MISC_FEATURE
<222> LOCATION: (4)..(4)
<223> OTHER INFORMATION: DABA
<220> FEATURE:
<221> NAME/KEY: MISC_FEATURE
<222> LOCATION: (5)..(5)
<223> OTHER INFORMATION: ABA
<220> FEATURE:
<221> NAME/KEY: MISC_FEATURE
<222> LOCATION: (7)..(7)
<223> OTHER INFORMATION: DAPA
<220> FEATURE:
<221> NAME/KEY: MISC_FEATURE
<222> LOCATION: (9)..(9)
<223> OTHER INFORMATION: OHVal

<400> SEQUENCE: 2

Xaa Xaa Leu Xaa Xaa Thr Xaa Phe Val Asp
1               5                   10

<210> SEQ ID NO 3
<211> LENGTH: 10
<212> TYPE: PRT
<213> ORGANISM: Pedobacter sp. UP508
<220> FEATURE:
<221> NAME/KEY: MISC_FEATURE
<222> LOCATION: (1)..(1)
<223> OTHER INFORMATION: 3-hydroxy-11-methyldodecanoyl
<220> FEATURE:
<221> NAME/KEY: MISC_FEATURE
<222> LOCATION: (2)..(2)
<223> OTHER INFORMATION: DAPA
<220> FEATURE:
<221> NAME/KEY: MISC_FEATURE
<222> LOCATION: (4)..(4)
<223> OTHER INFORMATION: DABA
<220> FEATURE:
<221> NAME/KEY: MISC_FEATURE
<222> LOCATION: (5)..(5)
<223> OTHER INFORMATION: ABA
<220> FEATURE:
<221> NAME/KEY: MISC_FEATURE
<222> LOCATION: (7)..(7)
<223> OTHER INFORMATION: DAPA

<400> SEQUENCE: 3

Xaa Xaa Leu Xaa Xaa Thr Xaa Phe Val Asp
1               5                   10

<210> SEQ ID NO 4
<211> LENGTH: 10
<212> TYPE: PRT
<213> ORGANISM: Pedobacter sp.UP508
<220> FEATURE:
<221> NAME/KEY: MISC_FEATURE
```

```
<222> LOCATION: (1)..(1)
<223> OTHER INFORMATION: 3-hydroxy-11-methyldodecanoyl
<220> FEATURE:
<221> NAME/KEY: MISC_FEATURE
<222> LOCATION: (4)..(4)
<223> OTHER INFORMATION: DABA
<220> FEATURE:
<221> NAME/KEY: MISC_FEATURE
<222> LOCATION: (5)..(5)
<223> OTHER INFORMATION: ABA
<220> FEATURE:
<221> NAME/KEY: MISC_FEATURE
<222> LOCATION: (7)..(7)
<223> OTHER INFORMATION: DAPA

<400> SEQUENCE: 4

Xaa Asn Leu Xaa Xaa Thr Xaa Phe Val Asp
1               5                   10

<210> SEQ ID NO 5
<211> LENGTH: 10
<212> TYPE: PRT
<213> ORGANISM: Pedobacter sp. UP508
<220> FEATURE:
<221> NAME/KEY: MISC_FEATURE
<222> LOCATION: (1)..(1)
<223> OTHER INFORMATION: 3-hydroxydodec-5-enoyl
<220> FEATURE:
<221> NAME/KEY: MISC_FEATURE
<222> LOCATION: (2)..(2)
<223> OTHER INFORMATION: DAPA
<220> FEATURE:
<221> NAME/KEY: MISC_FEATURE
<222> LOCATION: (4)..(4)
<223> OTHER INFORMATION: DABA
<220> FEATURE:
<221> NAME/KEY: MISC_FEATURE
<222> LOCATION: (5)..(5)
<223> OTHER INFORMATION: ABA
<220> FEATURE:
<221> NAME/KEY: MISC_FEATURE
<222> LOCATION: (7)..(7)
<223> OTHER INFORMATION: DAPA
<220> FEATURE:
<221> NAME/KEY: MISC_FEATURE
<222> LOCATION: (9)..(9)
<223> OTHER INFORMATION: OHVal

<400> SEQUENCE: 5

Xaa Xaa Leu Xaa Xaa Thr Xaa Phe Val Asp
1               5                   10
```

PEPTIDE COMPOUNDS

CROSS REFERENCE TO RELATED APPLICATION

This application is a 35 U.S.C. 371 National Phase Entry Application from PCT/SE2019/050789 filed Aug. 27, 2019, which claims the benefit of Swedish Patent Application Nos. 1851022-2 filed on Aug. 28, 2018 and 1950877-9 filed on Jul. 10, 2019, the disclosures of which are incorporated herein in their entirety by reference.

The instant application contains a Sequence Listing which has been submitted via EFS-Web and is hereby incorporated by reference in its entirety. Said Sequence Listing, created on Aug. 14, 2018, is named P12011SE Sequence Listing—2018-08-14_ST25.txt and is 3 kilobytes in size.

TECHNICAL FIELD

This invention relates to the area of peptides, and especially to peptides useful in antibacterial compounds. More specifically, the invention relates to a compound including at least one cyclic or non-cyclic peptide as well as methods of treating, eliminating and/or preventing a Gram-negative or Gram-positive bacterial infection in a subject using such compound(s).

BACKGROUND

Antibiotic resistant bacteria and fungi pose a serious threat to global health and there is an urgent need to develop novel antibiotics against priority human pathogens. The World Health Organization (WHO) recently published the Priority Pathogens List, which suggests "Drug discovery and development strategies should focus urgently on new antibiotics specifically active against *Mycobacterium tuberculosis* (including multi- and extensively drug-resistant strains) and against multi- and extensively drug-resistant Gram-negative bacteria that cause acute clinical infections in both hospital and community settings worldwide." Among the Gram-negative bacteria, the highest priority was given to carbapenem resistant *Acinetobacter baumannii*, *Pseudomonas aeruginosa* and Enterobacteriaceae. Rational drug design and synthesis against selected "druggable" targets as well as high-throughput screening of large synthetic combinatorial libraries have not been as successful at producing novel classes of antibiotics as anticipated. Harvey, A. L. et al. (2015) *Nat Rev Drug Discov* 14: 111-129 present theoretical analysis that shows that natural products, which have evolved to penetrate into their target bacterial cells and to avoid subsequent expulsion, cover more chemical space compared to synthetic combinatorial libraries in terms of compound lipophilicity, size, rigidity and aromaticity. Recent efforts at antibiotics discovery have thus returned to mining the wealth of antimicrobial compounds produced by bacteria and fungi.

There is a wealth of natural secondary metabolites of many different types that is, and has been, used as medicinal drugs. The first and probably most prominent example is the antibiotic drug penicillin G, produced by fungi of the genus *Penicillium*, and was brought to the market more than 70 years ago. The penicillins belong to a group of compounds called non-ribosomal peptides (NRPs), and in addition to the penicillins, there are many NRPs that have been developed into important antibiotic drugs, for example the related cephalosporins, the vancomycins and daptomycin.

U.S. Pat. No. 4,537,717 (Eli Lilly Company) describes daptomycin, which is an NRP based on 13 amino acids with a fatty acid linked to the N-terminal amino acid, and a lactone between the C-terminal amino acid and a threonine residue, forming a 31-membered ring. This group of compounds are cyclic lipodepsipeptides. Daptomycin was approved by the FDA in 2003 for use against Gram-positive bacterial infections, and it has been described to disrupt several functions of bacterial cell membranes.

There are numerous microbial cyclic lipodepsipeptides with structures similar to daptomycin, i.e. 31-membered lactones formed as esters between the C-terminal amino acid and a threonine or serine residue, and with an N-terminal fatty acyl residue. An alternative mode of lactone formation to obtain a cyclic 31-membered lipodepsipeptide, is between the C-terminal amino acid and an N-terminal 3-hydroxyfatty acid residue. There are twelve examples of such structures in the literature: JP 05 200 324 describes the peptides B12489A-C, Kozuma, S. et al describes pedopeptin A-C (in Kozuma, S. et al., J. Antibiot., 2014, 67, 237-242; Hirota-Takahata, Y. et al., J. Antibiot., 2014, 67, 243-251), several publications describe pelgipeptins A-D (see e.g. Takahara, Y. et al., J. Antibiot., 1979, 32, 115-120, 121-129; Sugawara, K. et al., J. Antibiot., 1984, 37, 1257-1259; Murai, A. et al., J. Antibiot., 1985, 38, 1610-1613; Wu, X.-C. et al., FEMS Microbiol. Lett., 2010, 310, 32-38; Ding, R. et al., J. Microbiol. (Seoul, Repub. Korea), 2011, 49, 942-949; Cochrane, S. A. and Vederas, J. C. Medicinal Research Reviews, 36, No. 1, 4-31, 2016), and polypeptin A and B (McLeod, C., J. Bacteriol., 1948, 56, 749-754, Howell, S. F., J. Biol. Chem., 1950, 186, 863-877; Sogn, J. A., J. Med. Chem., 1976, 19, 1228-1231; CN102030819-A; CN102030819-B).

The peptides B12489A-C and the three pedopeptins were all isolated from *Pedobacter* sp., and the structures are very similar or identical, with differences in aa8, Val or 3-hydroxyvaline (OHVal), and in the 3-hydroxyfatty acid residue (3-hydroxyoctanoyl or 3-hydroxy-7-methyloctanoyl), and possibly also a difference in geometry of the 2-amino-2-butenoyl (ABA) residue and the configuration of some amino acid residues (aa1, 3, 5-7). The pedopeptins and B12489A-C have been described to have anti-inflammatory action by interfering the binding of bacterial lipopolysaccharides to receptors on cell surfaces, as well as antibacterial activities, with minimal inhibitory concentration (MIC) against *Escherichia coli*: 2-4 µg/mL and against *Staphylococcus aureus*: 4-64 µg/mL.

Pelgipeptin A-D and polypeptin A-B are similar to the pedopeptins and B12489-A-C, and these peptides have aa3 and aa5 in common, and similar amino acid residues on aa1, aa6, aa7 and aa8. Pelgipeptin A-D and polypeptin A-B differ from each other by exchange of a C-terminal serine (aa9) for threonine and isoleucine for valine (aa2), and also by the position of the methyl branching position on the N-terminal fatty acyl group (Table 1). The pelgipeptins and the polypeptins have been described to have activity against Gram-positive and negative bacteria, as well as against fungi.

Despite the above-described technologies, there is still an ongoing and increasing need of novel antibacterial preparations.

SUMMARY

The present invention relates to novel compounds, which have been identified from nature, characterized and synthesized; as well as use of said compounds preferably as antibacterial compounds or as part of pharmaceutical preparations. A first aspect of the invention is an isolated or synthesised compound comprising the formula (I) as presented below:

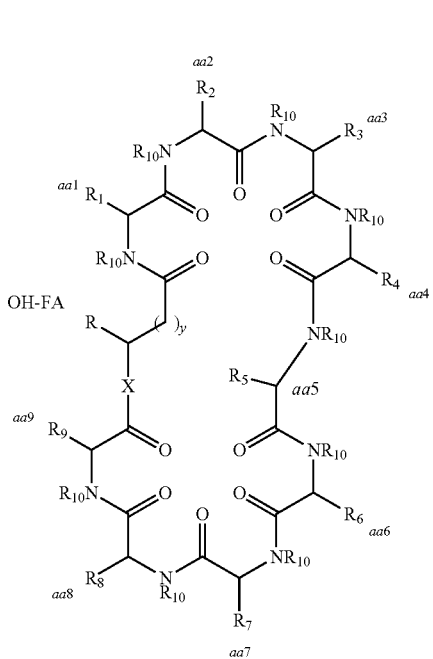

(I)

wherein
y: 0-5;
X: O, $NR_{10}$, or $(CH_2)_n$ with n=0 to 10, or $(OH)_2$;
R: $C_0$-$C_{20}$ n-alkyl with 0 to 5 $C_1$-$C_5$ n-alkyl branches or n-alkenyl with 0 to 5 $C_1$-$C_5$ n-alkyl branches; wherein double bonds may have E or Z configuration;
$R_1$: —$(CH_2)_n$—$NR_{11}R_{12}$, n=0 to 5, or —$(CH_2)_n$—$CONR_{11}R_{12}$, n=0 to 5, or —$(CH_2)_n$—COO—$(CH_2)$m-H, n=0 to 5 and m=0 to 5, each of which can have 0 to 5 $C_1$-$C_5$ n-alkyl branches;
$R_2$: $C_0$-$C_{20}$ n-alkyl with 0 to 5 $C_1$-$C_5$ n-alkyl branches or n-alkenyl with 0 to 5 $C_1$-$C_5$ n-alkyl branches, wherein double bonds may have E or Z configuration, $R_2$ and $R_7$ may exchange position with each other;
$R_3$: —$(CH_2)_n$—$NR_{11}R_{12}$, n=0 to 5, or —$(CH_2)_n$—$CONR_{11}R_{12}$, n=0 to 5, or —$(CH_2)_n$—COO—$(CH_2)_m$—H, n=0 to 5 and m=0 to 5, each of which can have 0 to 5 $C_1$-$C_5$ n-alkyl branches;
$R_4$: —$(CH_2)_n$—CH=C[$(CH_2)_m$—H]$(CH_2)_o$—H, with n=0 to 10, m=0 to 10, o=0 to 5, and with E or Z double bond, or =C[$(CH_2)_m$—H]$(CH_2)_o$—H, with m=0 to 10, o=0 to 5, with E or Z double bond;
$R_5$: $C_0$-$C_{20}$ n-alkyl with 0 to 5 $C_1$-$C_5$ n-alkyl branches or n-alkenyl with 0 to 5 $C_1$-$C_5$ n-alkyl branches; wherein double bonds may have E or Z configuration, and 0 to 2H may be exchanged to any combination of —$OR_{13}$, —$NR_{11}R_{12}$, —F, —Cl, —Br, —I, —$(CH_2)_o$—H with o=1 to 5;
$R_6$: —$(CH_2)_n$—$NR_{11}R_{12}$, n=0 to 5, or —$(CH_2)_n$—$CONR_{11}R_{12}$, n=0 to 5, or —$(CH_2)_n$—COO—$(CH_2)_m$—H, n=0 to 5 and m=0 to 5, each of which can have 0 to 5 $C_1$-$C_5$ n-alkyl branches;
$R_7$: —$(CH_2)_n$-Ph$(Y)_m$, with Y=any combination of —$OR_{13}$, —$NR_{11}R_{12}$, —F, —Cl, —Br, —I, —$(CH_2)_o$—H, and with n=0 to 5, m=0 to 5, and o=1 to 20; wherein $R_7$ and $R_2$ may exchange position with each other;
$R_8$: $C_0$-$C_{20}$ n-alkyl with 0 to 5 $C_1$-$C_5$ n-alkyl branches or $C_0$-$C_{20}$ n-alkenyl with 0 to 5 $C_1$-$C_5$ n-alkyl branches, wherein double bonds may have E or Z configuration and 0 to 2H may be exchanged to any combination of —$OR_{13}$, —$NR_{11}R_{12}$, —F, —Cl, —Br, —I, —$(CH_2)_o$—H with o=1 to 5;
$R_9$: —$(CH_2)_n$—$CONR_{11}R_{12}$ or —$(CH_2)_n$—COO—$(CH_2)_m$—H, n=0 to 5 and m=0 to 5;
$R_{10}$: —H, —$OR_{13}$, —$(CH_2)_o$—H with o=1 to 5, —F, —Cl, —Br, or —I, independently;
$R_{11}$ and $R_{12}$: any combination of —H, $C_1$-$C_5$ n-alkyl, and $C_1$-$C_5$ n-alkenyl, or any common N-protecting group; and
$R_{13}$: —$(CH_2)_n$—H, with n=0 to 5;
or an enantiomer, diastereomer, tautomer, or pharmaceutically acceptable salt thereof, wherein each stereocenter may be either R or S.

A second aspect of the invention is a method of producing a compound according to the invention. This aspect includes synthetic as well as recombinant methods; and tools for use therein such as intermediate peptides as well as expression systems.

A third aspect of the invention is the medical use of a compound according to the invention. Thus, a compound according to the invention may be used as a medicament, such as in the treatment or prevention of infections caused by Gram-positive and/or Gram-negative bacteria.

A fourth aspect of the invention is a method of treatment or prevention of infections caused by one or more Gram-positive and/or Gram-negative bacteria, wherein the herein described and claimed compound is administered to an individual in need thereof.

A fifth aspect of the invention is a pharmaceutical preparation comprising one or more of the herein described and claimed compounds combined with suitable carrier(s) and/or adjuvant(s).

A sixth aspect of the invention is the use of one or more of the herein described and claimed compounds in a method for decolonization of a surface of Gram-positive and/or Gram-negative bacteria.

DEFINITIONS

Figure 1:
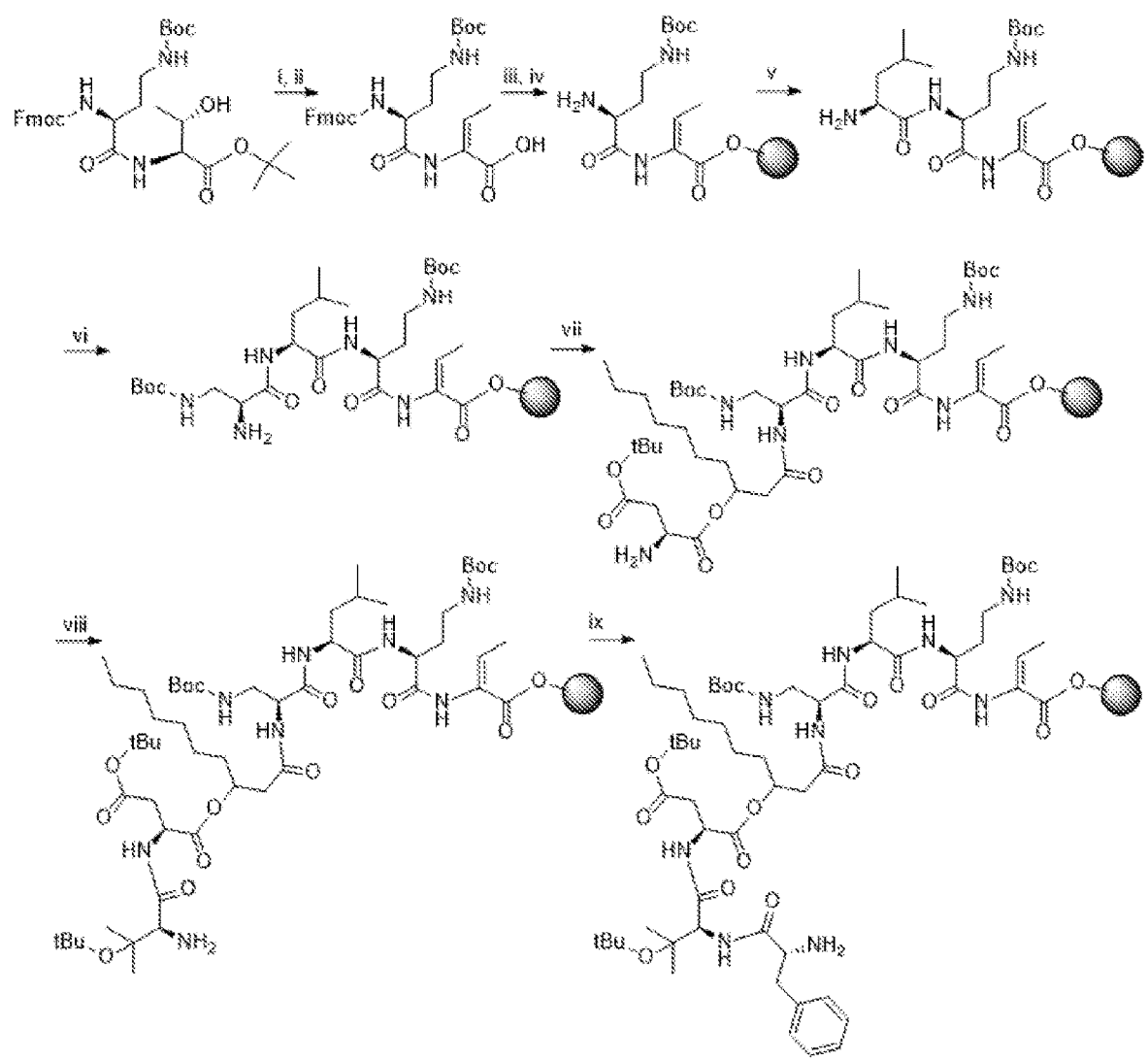
FIG. 1 is scheme 1, detailing Part I of the solid-phase synthesis of illustrative compound U747 according to the invention as described in Example 2 below.

The term "peptide" is used herein in its broadest aspect i.e. for any short chain of amino acid monomers linked by peptide (amide) bonds and includes e.g. depsipeptides and lipodepsipeptides.

A "depsipeptide" is a peptide in which one or more of its amide, —C(O)NHR—, groups are replaced by the corresponding ester, —C(O)OR, or more generally, is a molecule that has both peptide and ester linkages in proximity in the same amino acid-containing small molecule or chain.

The term "stereocenter" is used herein in its conventional meaning of a chirality center.

The term "DABA" refers herein to 2,4-d acid.

The term "ABA" refers herein to 2-amino-2-butenoic acid.

The term "DAPA" refers herein to 2,3-diaminopropanoic acid.

The term "Leu" refers herein to leucine.

The term "Thr" refers herein to threonine.

The term "Phe" refers herein to phenylalanine.

The term "Asp" refers herein to aspartic acid.

The term "Asn" refers herein to asparagine.

The term "Val" refers herein to valine.

The term "OHVal" refers herein to 3-hydroxyvaline.

The abbreviation aa is used herein for amino acid, and aa followed by a number indicates the number position of the aa starting from the N-terminal amino end of a peptide or protein.

The term "THF" refers to tetrahydrofuran.

The term "DCM" refers to dichloromethane.

The term "DMF" refers to N,N-dimethylformamide.

The term "TFA" refers to trifluoroacetic acid.

The term "HOBt" refers to hydroxybenzotriazole.

The term "HCTU" refers herein to 0-(1H-6-chlorobenzotriazole-1-yl)-1,1,3,3-tetramethyluronium hexafluorophosphate.

The term "DEPBT" refers to 3-(diethoxyphosphoryloxy)-1,2,3-benzotriazin-4(3H)-one.

The term "DIPEA" refers to N,N-diisopropylethylamine

The term "HFIP" refers to hexafluoroisopropanol.

The term "PyBOP" refers to benzotriazol-1-yloxy-tris-pyrrolidino-phosphonium hexafluorophosphate.

The term "PyClocK" refers to 6-chlorobenzotriazole-1-yloxy-tris-pyrrolidino-phosphonium hexafluorophosphate.

The term "TIPS" refers to triisopropylsilane.

The term "EDCl" refers to N-(3-dimethylaminopropyl)-N'-ethylcarbodiimide hydrochloride.

The term "DMAP" refers to 4-dimethylaminopyridine.

The term "DMEDA" refers to N,N'-dimethylethane-1,2-diamine.

DETAILED DESCRIPTION OF THE INVENTION

As appears from the above, the present invention relates to compounds comprising novel cyclic or non-cyclic peptides. More specifically, the invention relates to such peptide compounds, which may be depsipeptides, as such or as part of a composition or preparation.

Thus, a first aspect of the invention is a compound of Formula 1: isolated or synthesised compound comprising the formula (I) as presented below:

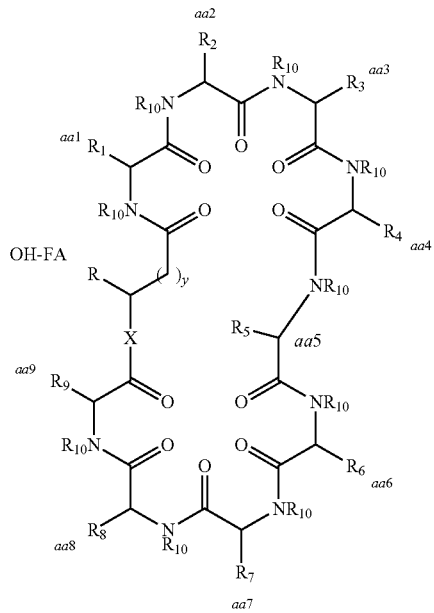

(I)

wherein
y: 0-5;
X: 0, $NR_{10}$, or $(CH_2)_n$ with n=0 to 10, or $(OH)_2$;
R: $C_0$-$C_{20}$ n-alkyl with 0 to 5 $C_1$-$C_5$ n-alkyl branches or n-alkenyl with 0 to 5 $C_1$-$C_5$ n-alkyl branches; wherein double bonds may have E or Z configuration;
$R_1$: —$(CH_2)_n$—$NR_{11}R_{12}$, n=0 to 5, or —$(CH_2)_n$—$CONR_{11}R_{12}$, n=0 to 5, or —$(CH_2)_n$—COO—$(CH_2)_m$—H, n=0 to 5 and m=0 to 5, each of which can have 0 to 5 $C_1$-$C_5$ n-alkyl branches;
$R_2$: $C_0$-$C_{20}$ n-alkyl with 0 to 5 $C_1$-$C_5$ n-alkyl branches or n-alkenyl with 0 to 5 $C_1$-$C_5$ n-alkyl branches, wherein double bonds may have E or Z configuration, $R_2$ and $R_7$ may exchange position with each other;
$R_3$: —$(CH_2)_n$—$NR_{11}R_{12}$, n=0 to 5, or —$(CH_2)_n$—$CONR_{11}R_{12}$, n=0 to 5, or —$(CH_2)_n$—COO—$(CH_2)_m$—H, n=0 to 5 and m=0 to 5, each of which can have 0 to 5 $C_1$-$C_5$ n-alkyl branches;
$R_4$: —$(CH_2)_n$—CH=C[$(CH_2)_m$—H]$(CH_2)_o$—H, with n=0 to 10, m=0 to 10, o=0 to 5, and with E or Z double bond, or =C[$(CH_2)_m$—H]$(CH_2)_o$—H, with m=0 to 10, o=0 to 5, with E or Z double bond;
$R_5$: $C_0$-$C_{20}$ n-alkyl with 0 to 5 $C_1$-$C_5$ n-alkyl branches or n-alkenyl with 0 to 5 $C_1$-$C_5$ n-alkyl branches; wherein double bonds may have E or Z configuration, and 0 to 2H may be exchanged to any combination of —$OR_{13}$, —$NR_{11}R_{12}$, —F, —Cl, —Br, —I, —$(CH_2)_o$—H with o=1 to 5;
$R_6$: —$(CH_2)_n$—$NR_{11}R_{12}$, n=0 to 5, or —$(CH_2)_n$—$CONR_{11}R_{12}$, n=0 to 5, or —$(CH_2)_n$—COO—$(CH_2)_m$—H, n=0 to 5 and m=0 to 5, each of which can have 0 to 5 $C_1$-$C_5$ n-alkyl branches;
$R_7$: —$(CH_2)_n$-Ph$(Y)_m$, with Y=any combination of —$OR_{13}$, —$NR_{11}R_{12}$, —F, —Cl, —Br, —I, —$(CH_2)_o$—H, and with n=0 to 5, m=0 to 5, and o=1 to 20, wherein $R_2$ and $R_7$ may exchange position with each other;
$R_8$: $C_0$-$C_{20}$ n-alkyl with 0 to 5 $C_1$-$C_5$ n-alkyl branches or $C_0$-$C_{20}$ n-alkenyl with 0 to 5 $C_1$-$C_5$ n-alkyl branches, wherein double bonds may have E or Z configuration and 0 to 2H may be exchanged to any combination of —$OR_{13}$, —$NR_{11}R_{12}$, —F, —Cl, —Br, —I, —$(CH_2)_o$—H with o=1 to 5;

$R_9$: —$(CH_2)_n$—$CONR_{11}R_{12}$ or —$(CH_2)_n$—COO—$(CH_2)_m$—H, n=0 to 5 and m=0 to 5;

$R_{10}$: —H, —$OR_{13}$, —$(CH_2)_o$—H with o=1 to 5, —F, —Cl, —Br, or —I, independently;

$R_{11}$ and $R_{12}$: any combination of —H, $C_1$-$C_5$ n-alkyl, and $C_1$-$C_5$ n-alkenyl, or any common N-protecting group; and $R_{13}$: —$(CH_2)_n$—H, with n=0 to 5.

As the skilled person will appreciate, in the case where X: $(OH)_2$, the claimed compound will be a non-cyclic peptide.

As will be discussed in relation to the various aspects of the invention, the compound according to the invention may be represented by Formula I above, or, alternatively, it may be a stereoisomer, a tautomer, a pharmaceutically acceptable salt, or a prodrug thereof.

Further, as will be discussed below in relation to the method of preparation, the compound according to the invention may be obtained by peptide synthesis; by recombinant DNA technology; or by isolation from sources in nature.

The compound(s) of the invention, where X: O and y: 0, 1, or 2, are cyclic depsipeptides with an ester between a C-terminal amino acid either to a 2-hydroxyfatty acid, forming a 30-membered cyclic structure; to a 3-hydroxyfatty acid, forming a 31-membered cyclic structure; or to a 4-hydroxyfatty acid, forming a 32-membered cyclic structure.

In some compounds of the invention, with X: $(OH)_2$, the peptides are non-ring-closed.

Some compounds of the invention, where X: NH, are cyclic peptides which are ring-closed from the C-terminal amino acid by a peptide bond to aa0; or to an amino-substituted fatty acid residue.

In further compounds of the invention, cyclic depsipeptides or cyclic peptides have singly/multiply exchanged $R_{10}$: —H to $R_{10}$: —OH and/or —$CH_3$.

In one compound of the invention, Y, X, and R—$R_{13}$ are chosen such that the compound comprises one 3-hydroxy fatty acid, and the amino acid residues 2,3-diaminopropanoic acid (DAPA, aa1 and aa6), leucine (Leu, aa2), 2,4-diaminobutanoic acid (DABA, aa3), 2-amino-2-butenoic acid (ABA, aa4), threonine (Thr, aa5), phenylalanine (Phe, aa7), valine (Val) or 3-hydroxyvaline (OHVal, aa8), aspartic acid (Asp, aa9), forming a 31-membered cyclic lipodepsipeptide. Such a compound has the general structure cyclo(3-hydroxyalkanoyl-DAPA-Leu-DABA-ABA-Thr-DAPA-Phe-Val/OHVal-Asp).

In further compounds comprising the general structure cyclo(3-hydroxyalkanoyl-DAPA-Leu-DABA-ABA-Thr-DAPA-Phe-Val/OHVal-Asp), there are single or multiple side-chain N- and/or O-substitutions with alkyl groups, or common N- or O-protecting groups, and/or —$NH_2$ or —OH substitutions on the Phe residue.

One illustrative compound of the invention, which will be denoted U747 herein, has y: 1; X: 0; R: n-heptyl; $R_1$: —$CH_2$—$NH_2$; $R_2$: —$CH_2$—$CH(CH_3)$—$CH_3$; $R_3$: —$CH_2$—$CH_2$—$NH_2$; $R_4$: (E)=CH—$CH_3$; $R_5$: CHOH—$CH_3$; $R_6$: —$CH_2$—$NH_2$; $R_7$: —$CH_2$-Ph; $R_8$: —$COH(CH_3)$—$CH_3$; $R_9$: —$CH_2$—COOH; and $R_{10}$, $R_{11}$, $R_{12}$ and $R_{13}$: H. This compound is a cyclic lipodepsipeptide (31-membered lactone), with ring-closure from the C-terminal L-Asp residue to a 3-hydroxydecanoyl residue and with the sequence cyclo-((R)-3-hydroxydecanoyl-L-DAPA-L-Leu-L-DABA-(E)-ABA-L-Thr-L-DAPA-D-Phe-L-OHVal-L-Asp).

As the skilled person will appreciate, a large number of minor variations to the basic structure described herein may be performed without deviating from the invention. Thus, the present invention will embrace any compound that fulfill the criteria of Formula (I) and presents the herein discussed advantageous properties when exposed to pathogens.

Another illustrative compound of the invention, which will be denoted U773 herein, has y: 1; X: 0; R: 8-methylnonyl; $R_1$: —$CH_2$—$NH_2$; $R_2$: —$CH_2$—$CH(CH_3)$—$CH_3$; $R_3$: —$CH_2$—$CH_2$—$NH_2$; $R_4$: (E)=CH—$CH_3$; $R_5$: CHOH—$CH_3$; $R_6$: —$CH_2$—$NH_2$; $R_7$: —$CH_2$-Ph; $R_8$: —COH$(CH_3)$—$CH_3$; $R_9$: —$CH_2$—COOH; and $R_{10}$, $R_{11}$, $R_{12}$ and $R_{13}$: H. This compound is a cyclic lipodepsipeptide (31-membered lactone), with ring-closure to a 3-hydroxy-11-methyldodecanoyl residue and with the sequence cyclo-((R)-3-hydroxy-11-methyldodecanoyl-L-DAPA-L-Leu-L-DABA-ABA-L-Thr-L-DAPA-D-Phe-L-OHVal-L-Asp).

A further illustrative compound of the invention, which will be denoted U793 herein, has y: 1; X: 0; R: 8-methylnonyl; $R_1$: —$CH_2$—$NH_2$; $R_2$: —$CH_2$—$CH(CH_3)$—$CH_3$; $R_3$: —$CH_2$—$CH_2$—$NH_2$; $R_4$: (E)=CH—$CH_3$; $R_5$: CHOH—$CH_3$; $R_6$: —$CH_2$—$NH_2$; $R_7$: —$CH_2$-Ph; $R_8$: —$CH(CH_3)$—$CH_3$; $R_9$: —$CH_2$—COOH; and $R_{10}$, $R_{11}$, $R_{12}$ and $R_{13}$: H. This compound is a cyclic lipodepsipeptide (31-membered lactone), with ring-closure to a 3-hydroxy-11-methyldodecanoyl residue and with the sequence cyclo-((R)-3-hydroxy-11-methyldodecanoyl-L-DAPA-L-Leu-L-DABA-ABA-L-Thr-L-DAPA-D-Phe-L-Val-L-Asp).

Yet one illustrative compound of the invention, which will be denoted U824 herein, has y: 1; X: 0; R: 8-methylnonyl; $R_1$: —$CH_2$—CO—$NH_2$; $R_2$: —$CH_2$—$CH(CH_3)$—$CH_3$; $R_3$: —$CH_2$—$CH_2$—$NH_2$; $R_4$: (E)=CH—$CH_3$; $R_5$: CHOH—$CH_3$; $R_6$: —$CH_2$—$NH_2$; $R_7$: —$CH_2$-Ph; $R_8$: —$CH(CH_3)$—$CH_3$; $R_9$: —$CH_2$—COOH; and $R_{10}$, $R_{11}$, $R_{12}$ and $R_{13}$: H. This compound is a cyclic lipodepsipeptide (31-membered lactone), with ring-closure to a 3-hydroxy-11-methyldodecanoyl residue and with the sequence cyclo-((R)-3-hydroxy-11-methyldodecanoyl-L-Asn-L-Leu-L-DABA-ABA-L-Thr-L-DAPA-D-Phe-L-Val-L-Asp).

One additional compound of the invention, which will be denoted U756 herein, has y: 1; X: 0; R: 2-nonenyl; $R_1$: —$CH_2$—$NH_2$; $R_2$: —$CH_2$—$CH(CH_3)$—$CH_3$; $R_3$: —$CH_2$—$CH_2$—$NH_2$; $R_4$: (E)=CH—$CH_3$; $R_5$: CHOH—$CH_3$; $R_6$: —$CH_2$—$NH_2$; $R_7$: —$CH_2$-Ph; $R_8$: —$COH(CH_3)$—$CH_3$; $R_9$: —$CH_2$—COOH, and $R_{10}$, $R_{11}$, $R_{12}$ and $R_{13}$: H. This compound is a cyclic lipodepsipeptide (31-membered lactone), with ring-closure to a dodec-5-enoyl residue and with the sequence cyclo-((R)-3-hydroxydodec-5-enoyl-L-DAPA-L-Leu-L-DABA-ABA-L-Thr-L-DAPA-D-Phe-L-OHVal-L-Asp).

In further compounds of the invention, similar to the U747, U773, U793, U824, and U756 prototypes, the configuration of single/multiple amino acid residues are inversed, as well as the configuration of the 3-hydroxy fatty acids.

It has been noted, that in compounds similar to U747, with identical $R_1$-$R_{13}$, but different R, the cytotoxicity ($IC_{50}$) of the compounds increase with the length of the alkyl chains, e.g. R: $C_7H_{15}$ to $C_{10}H_{21}$.

It has also been noted, that in compounds similar to U747, with $R_1$ or $R_6$ exchanged from —$CH_2$—$NH_2$ to —$CH_2$—CO—$NH_2$, the antibacterial activity may be lower under certain conditions, i.e. higher MIC values. Further, it has also been noted, that in compounds similar to U747, but with R<$C_7H_{15}$, the antibacterial activity may be lower under certain conditions, i.e. higher MIC values.

As the skilled person will appreciate, when developing products based on peptides such as the ones described herein, routine optimization may be used to identify which specific structure is most advantageous for certain applications, such as in terms of effect against certain bacteria, and/or against certain medical conditions.

There are twelve cyclic lipodepsipeptides in the literature possessing a 31-membered macrocyclic lactone, with the ring-closure to a 3-hydroxyfatty acid, as discussed in the "Background of the invention", and with structures described in Table 1.

negative bacteria. The compound U747 has also been found to have potent activity against carbapenem resistant strains of *E. coli, P. aeruginosa* and *A. baumannii* (MICs between 0.5-1 µg/mL and 2-4 µg/mL), which are the human pathogens ranked by the WHO as the three most critical pathogens today.

Along with the very promising antibacterial properties of U747, this compound of the invention has also shown low toxicity ($IC_{50}$) against human cell lines, and acceptable haemolysis rates, but also a very low rate of formation of resistant mutants.

TABLE 1

Comparison of composition of the twelve known cyclic lipodepsipeptides with a 31-membered lactone to a 3-hydroxyfatty acid (OHFA), along with the composition of the novel cyclic lipodepsipeptide U747.

|  | B12489A | B12489B | B12489C | pedopeptin A | pedopeptin B | pedopeptin C | pelgipeptin A |
|---|---|---|---|---|---|---|---|
| OHFA | 7-MeOct | Oct | 7-MeOct | 7-MeOct | 7-MeOct | Oct | 5-MeHex |
| aa1 | DAPA | DAPA | DAPA | DAPA | DAPA | DAPA | L-DABA |
| aa2 | L-Phe | L-Phe | L-Phe | L-Phe | L-Phe | L-Phe | L-Val |
| aa3 | DABA | DABA | DABA | L-DABA | DABA | DABA | L-DABA |
| aa4 | Z-ABA | Z-ABA | Z-ABA | E-ABA | E-ABA | E-ABA | D-Phe |
| aa5 | L-Leu | L-Leu | L-Leu | Leu | Leu | Leu | L-Leu |
| aa6 | DAPA | DAPA | DAPA | DAPA | DAPA | DAPA | L-DABA |
| aa7 | L-Leu | L-Leu | L-Leu | Leu | Leu | Leu | D-Val |
| aa8 | L-Val | L-OHVal | L-OHVal | L-OHVal | L-Val | L-OHVal | L-Leu |
| aa9 | L-Asp | L-Asp | L-Asp | L-Asp | L-Asp | L-Asp | L-Ser |

|  | pelgipeptin B | pelgipeptin C | pelgipeptin D | polypeptin A | polypeptin B | U747 |
|---|---|---|---|---|---|---|
| OHFA | 4-MeHex | 4-MeHex | 5-MeHex | 4-MeHex | 5-MeHex | Dec |
| aa1 | L-DABA | L-DABA | L-DABA | L-DABA | L-DABA | L-DAPA |
| aa2 | L-Ile | L-Val | L-Ile | L-Ile | L-Ile | L-Leu |
| aa3 | L-DABA | L-DABA | L-DABA | L-DABA | L-DABA | L-DABA |
| aa4 | D-Phe | D-Phe | D-Phe | D-Phe | D-Phe | E-ABA |
| aa5 | L-Leu | L-Leu | L-Leu | L-Leu | L-Leu | L-Thr |
| aa6 | L-DABA | L-DABA | L-DABA | L-DABA | L-DABA | L-DAPA |
| aa7 | D-Val | D-Val | D-Val | D-Val | D-Val | D-Phe |
| aa8 | L-Leu | L-Leu | L-Leu | L-Leu | L-Leu | L-OHVal |
| aa9 | L-Ser | L-Ser | L-Ser | L-Thr | L-Thr | L-Asp |

Me = methyl, Oct = octanoyl, Hex = hexanoyl, Dec = decanoyl, DAPA = 2,3-diaminopropanoyl, DABA = 2,4-diaminobutanoyl, ABA = 2-amino-2-butenoyl, OHVal = 3-hydroxyvaline The peptides B12489A-C and pedopeptin A-C are very similar to each other, whereas pelgipeptin A-D and polypeptin A-B are very similar to each other. U747 is more similar to B12489A-C and pedopeptin A-C than to pelgipeptin A-D and polypeptin A-B, as U747 shares six of nine amino acids (same amino acid in the same position) with B12489A-C and pedopeptin A-C(aa1, 3, 4, 6, 8, 9), and only one amino acid, aa3, with pelgipeptin A-D and polypeptin A-B. However, U747 still differs substantially from B12489A-C and pedopeptin A-C, with aa2 and aa7 having switched positions and with a polar amino acid (Thr) as aa5 instead of a non-polar (Leu).

Pedopeptins A-C have been described to interact with the LPS of Gram-negative bacteria to exert its anti-inflammatory activity. Possibly, also the antibacterial properties of the pedopeptins depend on the interaction with LPS, and given the similarity of the compounds, it may be speculated that also U747 and similar compounds of this invention, interact with the LPS of Gram-negative bacteria. However, in its broad sense, the present invention is not limited by any definition of its mode of action.

Pedopeptin A-C were described to have MIC values of 2-4 µg/mL against two *E. coli* strains, which is similar to the MIC values for U747, and similar compounds of the invention, against *E. coli*, but also against many other Gram- In a second aspect, the invention relates to a method of producing any one of the herein defined compounds according to the invention.

Thus, the method may be a method of synthesis wherein a peptide comprising at least nine amino acids and including at least one first amino acid followed by the sequence of Leu; DABA; ABA; Thr; DAPA; Phe; Val; and Asp; wherein the first amino acid is DAPA or Asn is used as an intermediate.

More specifically, the intermediate may be a peptide as defined by any one of SEQ ID NOs: 1-5; or a longer peptide including such sequence. Thus, an intermediate useful in the synthesis of a compound according to the invention may be the above-mentioned peptide linked to a first amino acid which is DAPA or Asn. Further, the Val may have been modified with OH into OHVal.

Peptide synthesis may be performed using standard equipment, such as solid phase peptide synthesis, and instruments as well as suitable protocols are widely available from commercial sources. The skilled person may utilise conventional methods for ring-closing of the peptide, such as esterification or peptide bond formation. Two illustrative methods of producing a compound according to the invention will be provided below, as Examples 2 and 4.

Alternatively, the method of producing any one of the compounds according to the invention may include cultivation of a microorganism or recombinant DNA technology comprising the expression of parts or all of a compound as defined by any one of claims 1-6; or an intermediate peptide as discussed above.

Thus, the invention relates to a microorganism which is capable of expressing a compound according to the invention. More specifically, such a microorganism may belong to the genus *Pedobacter*. A particular microorganism according to the invention was deposited with BCCM-LMG on Jul. 3, 2018 in accordance with the Budapest Treaty, where it obtained patent deposit ref LMG P-30868.

Further, the invention also relates to a recombinant expression system arranged for the production of a compound according to the invention. The expression system may comprise a microorganism, such as a bacteria or a fungi, which has been modified by recombinant DNA technology To increase its production of compound according to the invention; to grow under certain circumstances; or any other conventional modification that improves or otherwise changes the native microorganism's function as an expression system More specifically, an expression system according to the invention may belong to the genus *Pedobacter*.

A particular expression system which is embraced by the present invention was deposited with BCCM-LMG on Jul. 3, 2018 as LMG P-30868.

Furthermore, a compound according to the invention may be produced by isolation from microorganisms such as bacteria which natively produces such cyclic peptide(s). One method of isolating bacteria for production of a compound according to the invention includes the steps of isolating it from a natural sample, such as soil or dirt. The actual isolation may be performed following standard protocols, such as Thaker, M. et al. (2013) *Nat Biotechnol* 31 (10): 922-929 or the like. A specific example of isolating a compound according to the invention from soil bacteria will be presented below, as Example 1.

In a third aspect, the present invention relates to one or more of the compounds according to the invention for use as a medicament, such as in the treatment or prevention of infections caused by one or more Gram-positive and/or Gram-negative bacteria.

The infections may be caused by one or more Gram-positive bacteria, such as Gram-positive bacteria selected from the group consisting of *Actinomyces; Bacillus; Clostridium; Corynebacterium; Enterococcus; Gardnerella; Lactobacillus; Listeria; Micrococcus*; Mycobacteria; *Nocardia; Staphylococcus*; and *Streptococcus*. Alternatively, or additionally, the infections may be caused by one or more Gram-negative bacteria, such as Gram-negative bacteria selected from the group consisting of *Acinetobacter; Batronella; Bordetella; Borrelia; Brucella; Burkholderia; Campylobacter; Chlamydia; Chlamydophilia; Citrobacter; Coxiella; Ehrlichia; Enterobacter; Escherichia; Francisella; Fusobacterium; Haemophilus; Helicobacter; Klebsiella; Legionella; Leptospira; Moraxella; Mycoplasma; Neisseria; Proteus; Pseudomonas; Rickettsia; Salmonella; Serratia: Shigella; Treponema; Vibrio*; and *Yersinia*.

In a fourth aspect, the invention relates to a method of treatment or prevention of infections caused by one or more Gram-positive and/or Gram-negative bacteria, in which method one or more of the compounds according to the present invention are used. The bacteria may be as discussed above in relation to the third aspect of the invention, or elsewhere in the present application. Thus, medical conditions that may be prevented and/or treated in accordance with the present invention may be selected from the group consisting of *Actinomyces; Bacillus; Clostridium; Corynebacterium; Enterococcus; Gardnerella; Lactobacillus; Listeria; Micrococcus; Mycobacteria; Nocardia; Staphylococcus; Streptococcus; Acinetobacter; Batronella; Bordetella; Borrelia; Brucella; Burkholderia; Campylobacter; Chlamydia; Chlamydophilia; Citrobacter; Coxiella; Ehrlichia; Enterobacter; Escherichia; Francisella; Fusobacterium; Haemophilus; Helicobacter; Klebsiella; Legionella*; Leptospira; *Moraxella; Mycoplasma; Neisseria; Proteus; Pseudomonas; Rickettsia; Salmonella; Serratia: Shigella; Treponema; Vibrio*; and *Yersinia*.

In a fifth aspect, the invention relates to a pharmaceutical preparation comprising one or more of the herein described and claimed compounds combined with one or more pharmaceutically acceptable carrier(s) and/or adjuvant(s). The carrier may be any solid or liquid carrier material which is compatible with the compound(s) according to the invention, and with any additional component included, which is suitable for therapeutic administration i.e. pharmaceutically acceptable. Thus, the carrier may be an organic or inorganic carrier material which is suitable for enteral (e.g. oral) or parenteral administration. Examples of such carrier materials are water, gelatin, lactose, starches, magnesium stearate, talc, vegetable oils, gum arabic, polyalkyleneglycols, petroleum jelly etc. The pharmaceutical preparations can be made up in a solid form (e.g. as tablets, dragees, suppositories, or capsules) or in a liquid form (e.g. as solutions, suspensions or emulsions).

The pharmaceutical preparations according to the invention may be prepared according to methods known in the art, may be subjected to conventional pharmaceutical operations such as sterilisation and may contain one or more adjuvants such as preserving agents, stabilising agents, wetting agents, emulsifying agents, salts for varying the osmotic pressure or buffers. When a buffer is used, the pH of the pharmaceutical preparation will, of course, vary within a range which is well-known in pharmaceutical practice.

The pharmaceutical preparation according to the invention may be used as iv formulations, oral formulations, topical formulations and other formulations giving an optimal effect against the disease causing bacteria, while at the same time giving minimal inhibition of harmless and beneficial bacteria.

The disease-causing bacteria against which the present preparation is medically effective are as discussed above, and may be selected from the group consisting of *Acinetobacter; Bacillus; Campylobacter; Chlamydia: Clostridium; Enterobacter; Enterococcus; Escherichia; Haemophilus; Helicobacter; Klebsiella; Legionella*; Mycobacteria; *Neisseria; Pseudomonas; Salmonella; Shigella; Staphylococcus; Streptococcus; Vibrio*; and *Yersinia*.

Advantageously, the preparation according to the invention is effective against one or more disease-causing bacteria which are resistant, and/or multiresistant, to antibiotics selected from the group consisting of aminoglycosides; ansamycins; carbapenems; cephalosporins; fluoroquinolons; glycopeptides; lincosamides; lipopeptides; macrolides; monobactams; nitrofurans; oxazolidinones; penicillin; polypeptides; quinolones; sulphonamides; and tetracyclines.

In a sixth aspect, the invention relates to the use of one or more of the herein described and claimed compounds in a method for decolonization of a surface of Gram-positive and/or Gram-negative bacteria. The surface may a body surface, or a part of clinical equipment, such as the surface of a metal or plastic article.

DETAILED DESCRIPTION OF THE DRAWINGS

FIG. 1 is scheme 1, detailing Part I of the solid-phase synthesis of illustrative compound U747 according to the invention. More specifically, scheme 1 includes i) Martin's sulfurane dehydrating reagent, ii) formic acid, iii) 2-chlorotrityl resin/collidine/DMF, iv) 20% piperidine/DMF, v) Fmoc-L-Leu/HCTU/DIPEA, vi) Fmoc-L-DAPA($N^\gamma$—Boc)/HCTU/DIPEA, vii) Fmoc-L-Asp(O-tBu)-O—CH[$(CH_2)_6$—$CH_3$]—$CH_2$—COOH/HCTU/DIPEA, viii) Fmoc-L-OHVal (O-tBu)/HCTU/DIPEA, ix) Fmoc-D-Phe/HCTU/DIPEA. After each coupling step, the Fmoc group is removed with 20% piperidine in DMF.

Figure 2:
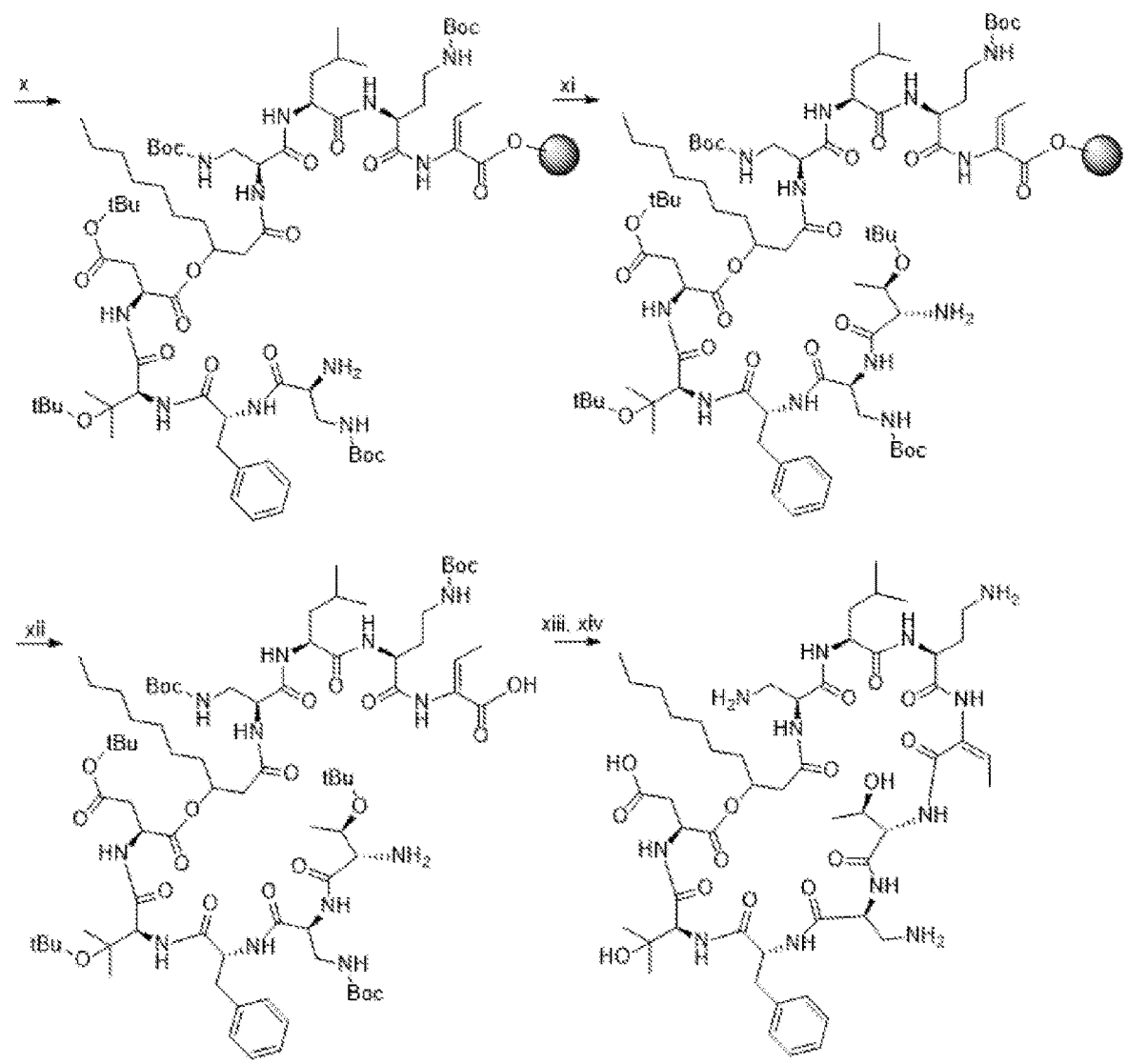
FIG. 2 is scheme 2, detailing Part II of the solid-phase synthesis of illustrative compound U747 as described in Example 2 below.

FIG. 2 is scheme 2, detailing Part II of the solid-phase synthesis of illustrative compound U747 according to the invention. More specifically, scheme 2 includes x) Fmoc-L-DAPA($N^\gamma$-Boc)/HCTU/DIPEA, xi) Fmoc-L-Thr(O-tBu)/HCTU/DIPEA, xii) 20% HFIP in DMF, xiii) PyclocK/DIPEA, xiv) TFA/TIPS. After each coupling step, the Fmoc group is removed with 20% piperidine in DMF.

Figure 3:
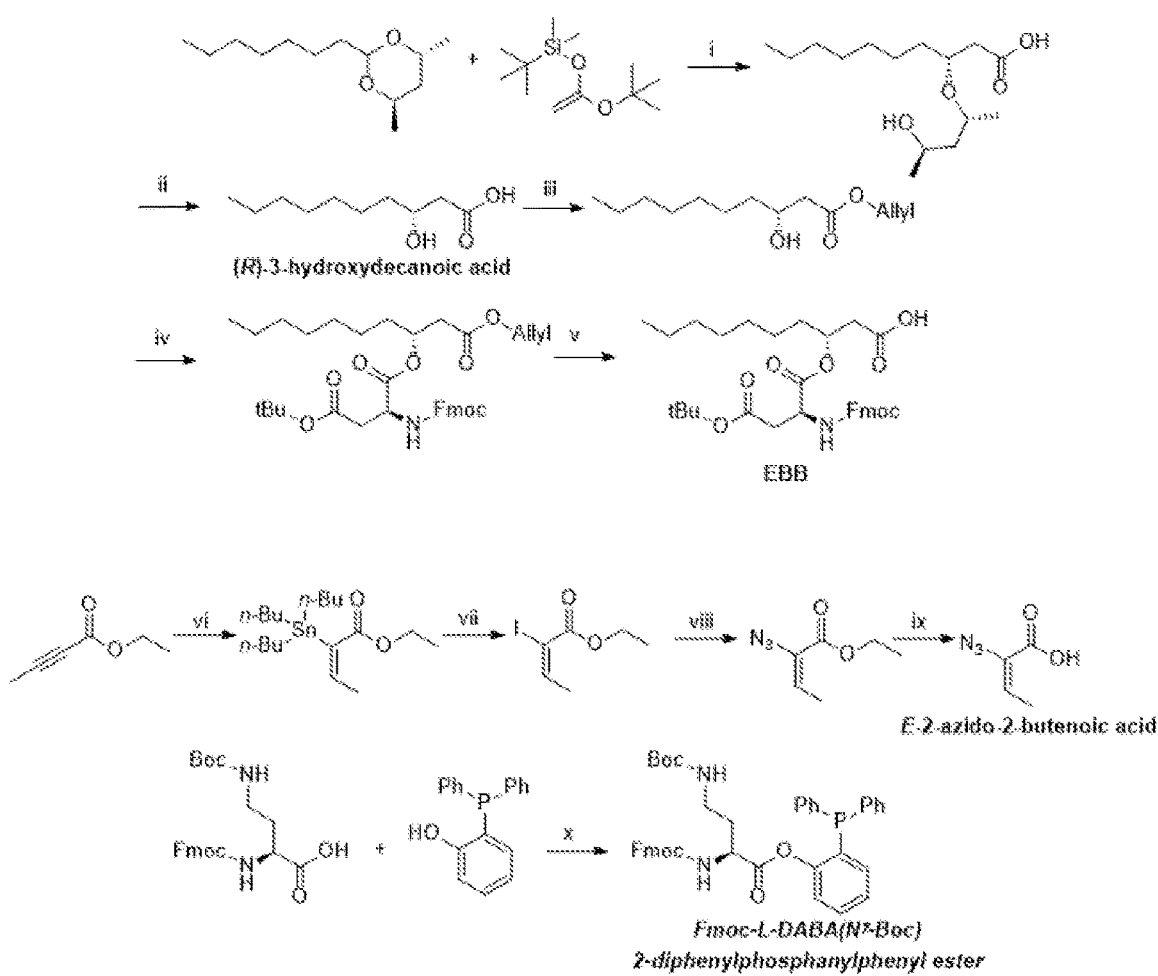
FIG. 3 is scheme 3, detailing the synthesis of building blocks for use in the alternative, stereospecific, solid-phase synthesis of illustrative compound U747 according to the invention as described in Example 4 below.

FIG. 3 is scheme 3, detailing Part I of the alternative, stereospecific, solid-phase synthesis of illustrative compound U747 according to the invention. More specifically, scheme 3 includes i) $TiCl_4$/DCM and then TFA/$H_2O$, ii) $CrO_3$/aq. $H_2SO_4$ and then KOH/MeOH, iii) allyl bromide/$K_2CO_3$/DMF, iv) Fmoc-L-Asp(OtBu)/EDCl/DMAP, v) Pd(PPh$_3$)$_4$/PhSiH$_3$/DCM, vi) Pd(PPh$_3$)$_4$/n-Bu$_3$SnH/THF, vii) $I_2$/DCM, viii) $NaN_3$/Na ascorbate/CuI/DMEDA/DMSO-$H_2O$, ix) LiOH/$H_2O$, x) EDCl/DMAP/DCM.

Figure 4:
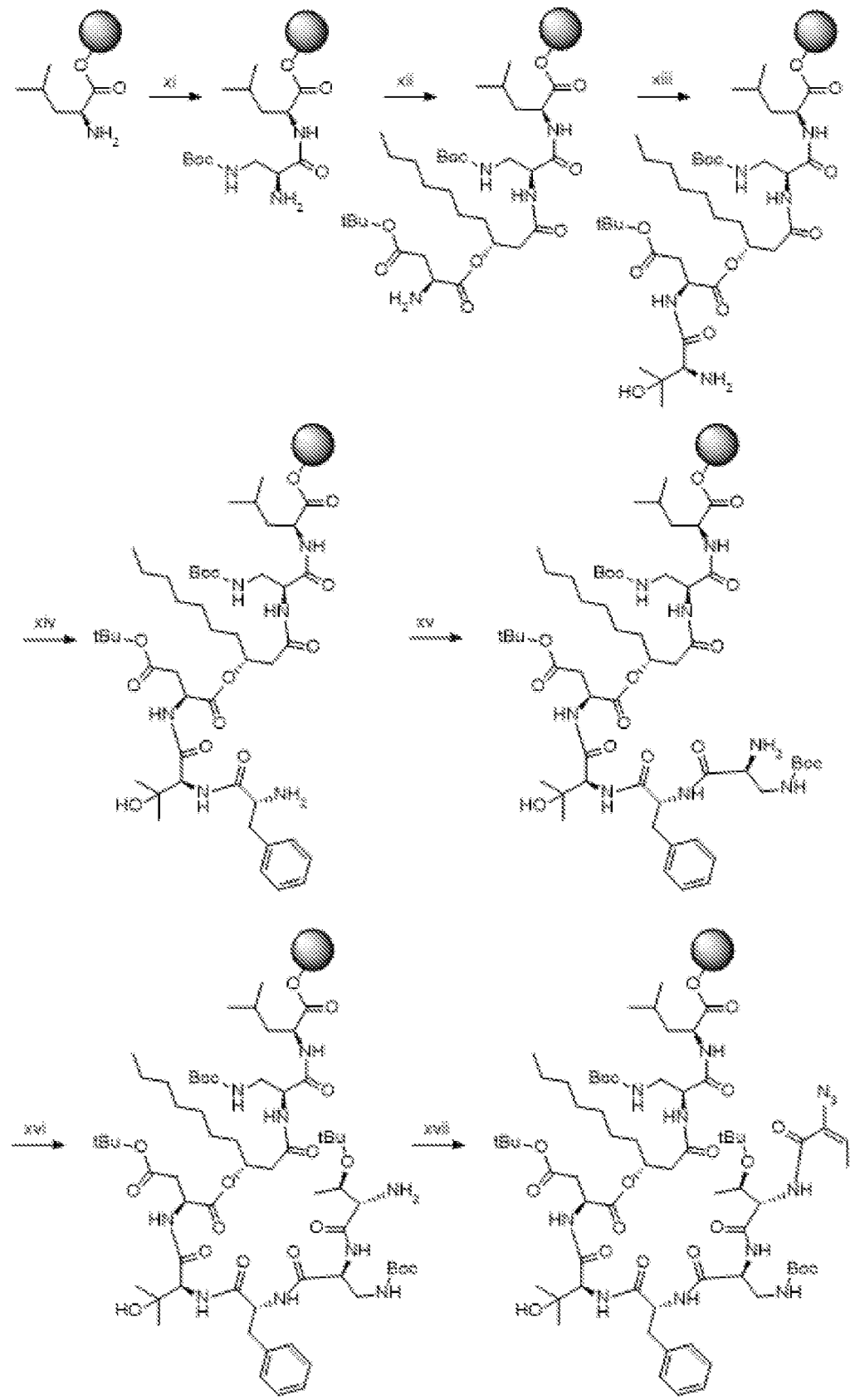
FIG. 4 is scheme 4, detailing part I of the alternative, stereospecific, solid-phase synthesis of illustrative compound U747 according to the invention as described in Example 4 below.

FIG. 4 is scheme 4, detailing Part II of the alternative, stereospecific, solid-phase synthesis of illustrative compound U747 according to the invention. More specifically, scheme 4 includes xi) Fmoc-L-DAPA($N^\gamma$-Boc)/PyBOP/HOBt/DIPEA, xii) EBB/PyBOP/HOBt/DIPEA, xiii) Fmoc-L-3-OHVal/PyBOP/HOBt/DIPEA, xiv) Fmoc-D-Phe/PyBOP/HOBt/DIPEA, xv) Fmoc-L-DAPA($N^\gamma$—Boc)/PyBOP/HOBt/DIPEA, xvi) Fmoc-L-Thr(O-tBu)/DEBPT/DIPEA, xvii) (E)-2-azido-2-butenoic acid/PyBOP/HOBt/DIPEA. After each coupling step, Fmoc is removed with 20% piperidine in DMF.

Figure 5:
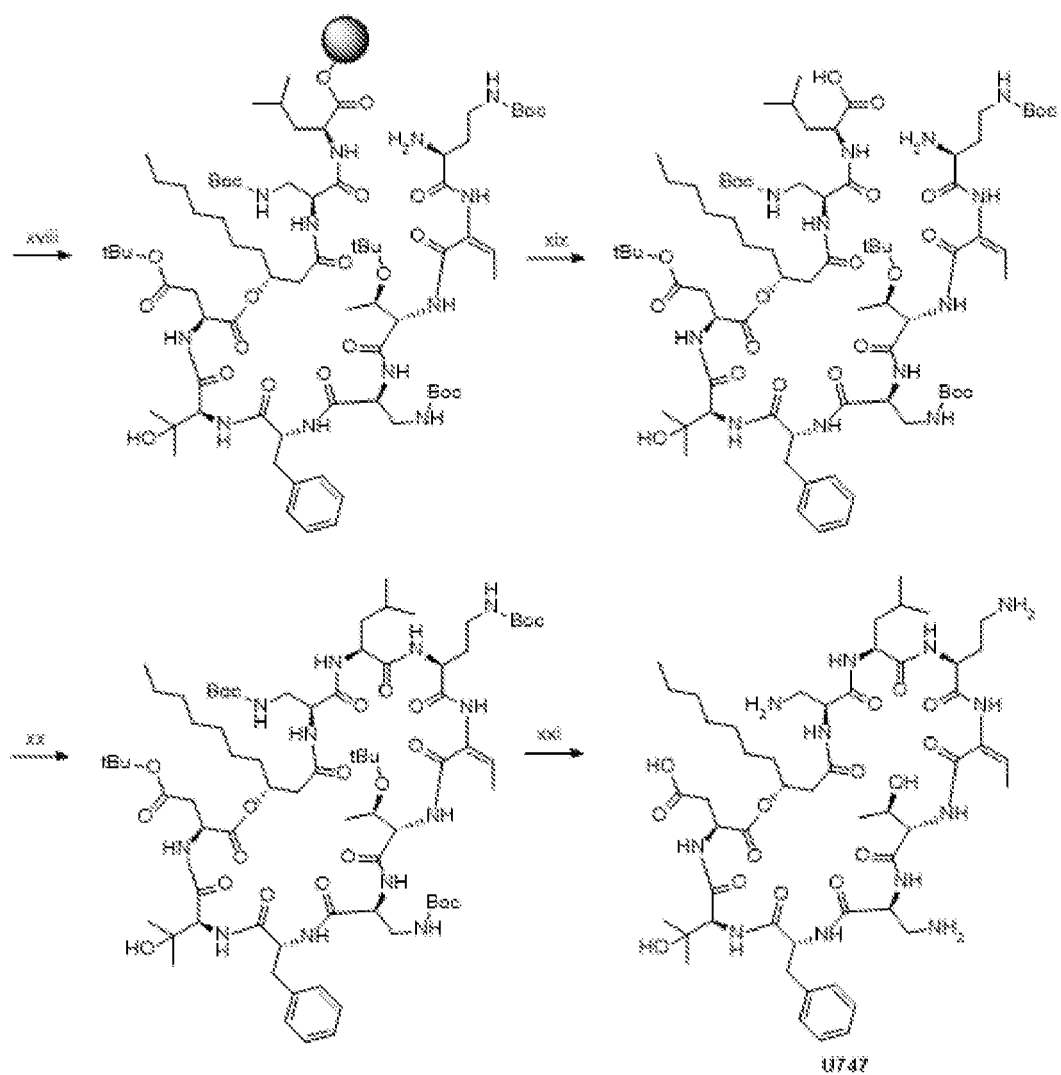
FIG. 5 is scheme 5, detailing part II of the alternative, stereospecific, solid-phase synthesis of illustrative compound U747 according to the invention as described in Example 4 below.

FIG. 5 is scheme 5, detailing Part III of the alternative, stereospecific, solid-phase synthesis of illustrative compound U747 according to the invention. More specifically, scheme 5 includes xviii) Fmoc-L-DABA($N^\delta$-Boc) 2-diphenylphophanylphenyl ester/THF-$H_2O$ and then 20% piperidine in DMF, xix) 20% HFIP, xx) PyBOP/HOBt/DIPEA/DMF, xxi) TFA/TIPS.

EXPERIMENTAL PART

The present examples are provided for illustrative purposes only, and are not intended to be limiting the invention as defined by the appended claims. All references provided below and elsewhere in the present application are hereby included herein via reference.

Example 1: Isolation and Identification of *Pedobacter* sp. UP508

The bacterial isolate, herein denoted UP508 (deposited with BCCM-LMG on Jul. 3, 2018, as LMG P-30868) was isolated from a soil sample collected at Ultuna, Uppsala, Sweden, based on a standard protocol. The isolate was identified as closest related to the strain A37 of *Pedobacter cryoconitis* or to the strain WB 3.3-22 of *Pedobacter westerhofensis* by sequencing 16 S rRNA.

Production of U747

The isolate *Pedobacter* sp. UP508 was cultivated in 32×1000-mL E-flasks, each with 300 mL of half strength Vegetable Peptone Broth (VPB; 15 g VPB (Oxoid Ltd) in 1000 mL deionized $H_2O$), on a rotary shaker (130 rpm) at 15° C. In order to collect U747 and other extracellular metabolites, 16 to 24 hours after inoculation, sterile cotton/paper bags with a polymeric resin Sepabeads® SP850 (Mitsubishi Chemical Corporation; approximately 10 g per bag) were submerged in actively growing cultures. After 6-7 days, the bags were removed, washed with deionized water and finally extracted with approximately 2×20 mL MeOH and 2×20 mL MeCN per bag. The pooled extract was dried under reduced pressure. The dried extract was dissolved in 40 mL aqueous 50% MeCN (0.2% formic acid), centrifuged (5 min at 13000 rpm), and injected (40×1 mL) onto a semi-preparative HPLC column (Phenomenex Luna Omega 5 µm PS C18, 100 Å; 100×21.2 mm), eluted with a two-step gradient of MeCN in water (15-50% in 15 min and 50-95% in 2 min, followed by 95% for 4 min, "HPLC1"), with 0.2% formic acid, at 10 mL/min. Fractions (2 mL) were collected in 2.2-mL deep-well plates and the chromatography was monitored by a UV-detector at 210 nm. The HPLC-fractions were analyzed by UHPLC-MS (0.5 µL; Accucore Vanquish C18+, 50×2.1 mm, 1.5 µm; 10-95% MeCN in 3 min and 1.2 min at 95% MeCN, 0.2% formic acid, 0.9 mL/min; Agilent 1290 Infinity II UHPLC and Bruker maXis Impact QTOF) in positive mode. Fractions 57-59, which contained the peptide U747 with $t_R$ 1.4 min and m/z 373.2143 (3+) (UHPLC-MS), were pooled and dried in a vacuum centrifuge. The dry residue was fractionated on the same semi-preparative column eluted with a linear gradient of MeCN in water (20-37.5% in 26 min, and 37.5-60% in 9 min, 0.2% formic acid, 10 mL/min, "HPLC2"). Fractions 54-61 which contained U747 (UHPLC-MS as above) were pooled and dried in a vacuum centrifuge, were further separated on the same column as above and using a gradient of MeCN in water (0.2% formic acid; 17.5-35% MeCN in 26 min and 35-57.5% in 9 min, "HPLC3"). Fractions 39-54 which contained U747 were pooled and dried in a vacuum centrifuge, and were subjected to one final round of HPLC on the same column (17.5-35% MeCN in 28 min and 35-57.5% in 7 min, 0.2% formic acid, 10 mL/min, "HPLC4"). Fractions 48-53, which contained U747, were pooled and dried in a vacuum centrifuge. Fractions with less pure U747 from HPLC3 were subjected to HPLC4 and additionally HPLC5 (same conditions as in HPLC4), and the fractions containing U747 were pooled and dried in a vacuum centrifuge. The total yield of U747 was 33 mg.

Other compounds of the invention were isolated using the same method, but with appropriate adaptations of the HPLC conditions used.

Structure Determination of U747 and Similar Compounds
NMR

U747 was dissolved in 0.6 mL DMSO-$d_6$ and was analyzed on a Bruker Avance-III NMR spectrometer, equipped with a 5-mm cryo-probe. The NMR data of U747 from 1D $^1$H and $^{13}$C NMR experiments, along with the 2D experiments $^1$H-$^1$H COSY, $^1$H-$^1$H TOCSY, HSQC-TOCSY, and $^1$H-$^{13}$C HSQC, suggested the presence of the following common amino acids: 1×Leu, 1×Thr, 1×Phe, and 1×Asp, and several non-standard amino acids. Subsequently, analysis of the NMR data suggested the presence of 2×2,3-diaminopropanoic acid (DAPA), 1×2,4-diaminobutanoic acid (DABA), 1×2-amino-2-butenoic acid (ABA), and 1×3-hydroxyvaline (OHVal). ROESY experiments proved the ABA to be present as (E)-ABA.

The NMR data also indicated the presence of a 3-hydroxydecanoic acid, and judging from the chemical shift of the β-CH, the 3-hydroxy function should be esterified, suggesting that a lactone is formed by an ester to this function. Finally, combination of ROESY and HMBC data suggested the structure of U747 to be cyclo(3-hydroxydecanoyl-DAPA-Leu-DABA-ABA-Thr-DAPA-Phe-OHVal-Asp).

MSMS.

To open the putative lactone of the peptide U747, a small sample (ca 50 μg) was treated with 1% NaOMe in 200 μL MeOH for 20 min at room temperature, and the solution was neutralized by 10 μL 2 M HCl (aq). The resulting sample was analyzed by UHPLC-MSMS (same instruments and column as above) using a gradient of MeCN in water (0.2% formic acid; 30-60% MeCN in 3 min, 0.9 mL/min). The ion at m/z 575.3287 (2+) corresponding to the linear ring-opened peptide U747 ($t_R$ 33 s) was selected for MSMS (21.5 eV). The fragment ion $B_1$ (with the N-linked 3-hydroxydecanoyl group), along with $B_2$-$B_8$, allowed a full sequence coverage, and confirmed the sequence proposed by NMR data.

Configuration of Amino Acids

U747 (0.5 mg) was dissolved in 200 μL 6 M HCl, and was treated in an evacuated glass vial over night at 120° C. The vial was opened and the solution dried under $N_2$. The configurations of the amino acids were subsequently determined using the advanced Marfey method (Fujii et al. 1997. Anal. Chem. 69, 5146-5151.). Derivatized samples were analyzed by UHPLC-MS (column as above, 20-50% MeCN in 6 min, 0.9 mL/min, 0.2% formic acid) and by comparison with authentic reference samples, the amino acids were determined to be L-Thr, L-OHVal, L-Asp, L-Leu, D-Phe, 2×L-DAPA and L-DABA.

Configuration of the 3-hydroxy Fatty Acid

The configuration of the 3-hydroxy fatty acid part of the peptides of the invention was determined on prototype U752, using the modified Mosher's method (Ohtani et al, J. Am. Chem. Soc. 1991, 113, 4092-4096). U752 (6 mg) was dissolved in 200 μL 6 M HCl, and was treated at 120° C. in an evacuated glass vial for 6 h. After cooling, the vial was opened and the contents were dried under $N_2$. The residues were partitioned between EtOAc and water and the EtOAc extract was dried under $N_2$. The sample (ca 0.5 mg) was dissolved in 1.2 mL pyridine-$d_5$ and the solution was split into two equal portions (ca 1.2 μmol each) in 1.5-mL glass vials. Each sample was treated with 5 μL R- or S-MTPA-Cl (3,3,3-trifluoro-2-methoxy-2-phenylpropanoyl chloride, ca 27 μmol each, ca 22-fold excess) at room temperature to produce the S- and R-MTPA ester, resp., of the fatty acid. After 6 h the samples were analysed by NMR, and the chemical shifts of $H_2$-2, $H_2$-4 and $H_2$-5, were determined for the two diastereomeric samples. Finally, the differences between the above chemical shifts for the S- and R-MTPA esters were calculated, and the configuration of the 3-hydroxy fatty acid of U752 was determined to be R, and this configuration appears to be the same in all peptides of the invention including U747.

Thus, the structure of U747 was determined to be cyclo ((R)-3-hydroxydecanoyl-L-DAPA-L-Leu-L-DABA-(E)-ABA-L-Thr-L-DAPA-D-Phe-L-OHVal-L-Asp). The structures of other compounds of the invention were determined using a combination of NMR, MSMS and the advanced Marfey's method, as needed.

TABLE 2

The structures of U747 and other compounds of the invention.

| name | R | aa-1 | aa-2 | aa-3 | aa-4 | aa-5 | aa-6 | aa-7 | aa-8 | aa-9 |
| --- | --- | --- | --- | --- | --- | --- | --- | --- | --- | --- |
| U733 | $C_6H_{13}$ | DAPA | Leu | DABA | ABA | Thr | DAPA | Phe | OHVal | Asp |
| U736 | $C_6H_{13}$ | DAPA | Leu | DABA | ABA | Thr | DAPA | Phe | OHVal | Asp |
| U737 | $C_6H_{13}$ | DAPA | Leu | DABA | ABA | Thr | DAPA | Phe | OHVal | Asp |
| U741 | $C_6H_{13}$ | DAPA | Leu | DABA | ABA | Thr | DAPA | Phe | OHVal | Asp |
| U744 | $C_7H_{15}$ | DAPA | Leu | DABA | ABA | Thr | DAPA | Phe | OHVal | Asp |
| U747 | $C_7H_{15}$ | DAPA | Leu | DABA | ABA | Thr | DAPA | Phe | OHVal | Asp |
| U749 | $C_7H_{15}$ | DAPA | Leu | DABA | ABA | Thr | DAPA | Phe | OHVal | Asp |
| U751 | $C_8H_{17}$ | DAPA | Leu | DABA | ABA | Thr | DAPA | Phe | OHVal | Asp |
| U752 | $C_8H_{17}$ | DAPA | Leu | DABA | ABA | Thr | DAPA | Phe | OHVal | Asp |
| U753 | $C_7H_{15}$ | DAPA | Leu | DABA | ABA | Thr | DAPA | Phe | OHVal | Asp |
| U754 | $C_8H_{17}$ | DAPA | Leu | DABA | ABA | Thr | DAPA | Phe | OHVal | Asp |
| U755a | $C_8H_{17}$ | DAPA | Leu | DABA | ABA | Thr | DAPA | Phe | OHVal | Asp |
| U755b | $C_8H_{17}$ | DAPA | Leu | DABA | ABA | Thr | DAPA | Phe | OHVal | Asp |
| U756 | $C_9H_{17}$ | DAPA | Leu | DABA | ABA | Thr | DAPA | Phe | OHVal | Asp |
| U757 | $C_9H_{17}$ | DAPA | Leu | DABA | ABA | Thr | DAPA | Phe | OHVal | Asp |
| U758 | $C_8H_{17}$ | DAPA | Leu | DABA | ABA | Thr | DAPA | Phe | OHVal | Asp |
| U765 | $C_8H_{17}$ | DAPA | Leu | DABA | ABA | Thr | DAPA | Phe | Val | Asp |
| U771 | $C_9H_{17}$ | DAPA | Leu | DABA | ABA | Thr | DAPA | Phe | Val | Asp |
| U773 | $C_{10}H_{21}$ | DAPA | Leu | DABA | ABA | Thr | DAPA | Phe | OHVal | Asp |
| U775 | $C_9H_{17}$ | DAPA | Leu | DABA | ABA | Thr | DAPA | Phe | Val | Asp |
| U787 | $C_{10}H_{21}$ | DAPA | Leu | DABA | ABA | Thr | DAPA | Phe | Val | Asp |
| U793 | $C_{10}H_{21}$ | DAPA | Leu | DABA | ABA | Thr | DAPA | Phe | Val | Asp |
| U794 | $C_{10}H_{21}$ | DAPA | Leu | DABA | ABA | Thr | DAPA | Phe | Val | Asp |
| U800 | $C_{10}H_{21}$ | DAPA | Leu | DABA | ABA | Thr | DAPA | Phe | Val | Asp |
| U802 | $C_9H_{19}$ | Asn | Leu | DABA | ABA | Thr | DAPA | Phe | OHVal | Asp |
| U809 | $C_8H_{17}$ | Asn | Leu | DABA | ABA | Thr | DAPA | Phe | Val | Asp |
| U810 | $C_{10}H_{21}$ | Asn | Leu | DABA | ABA | Thr | DAPA | Phe | OHVal | Asp |
| U824 | $C_{10}H_{21}$ | Asn | Leu | DABA | ABA | Thr | DAPA | Phe | OHVal | Asp |
| U826 | $C_9H_{17}$ | DAPA | Leu | DABA | ABA | Thr | Asn | Phe | Val | Asp |
| U828 | $C_{10}H_{21}$ | Asn | Leu | DABA | ABA | Thr | DAPA | Phe | Val | Asp |
| U829 | $C_{10}H_{21}$ | Asn | Leu | DABA | ABA | Thr | DAPA | Phe | OHVal | Asp |
| U833 | $C_9H_{17}$ | DAPA | Leu | DABA | ABA | Thr | Asn | Phe | Val | Asp |

TABLE 2-continued

The structures of U747 and other compounds of the invention.

| name | R | aa-1 | aa-2 | aa-3 | aa-4 | aa-5 | aa-6 | aa-7 | aa-8 | aa-9 |
|---|---|---|---|---|---|---|---|---|---|---|
| U834 | $C_9H_{19}$ | Asn | Leu | DABA | ABA | Thr | DAPA | Phe | Val | Asp |
| U840 | $C_9H_{19}$ | DAPA | Leu | DABA | ABA | Thr | Asn | Phe | Val | Asp |
| U842 | $C_{10}H_{21}$ | Asn | Leu | DABA | ABA | Thr | DAPA | Phe | Val | Asp |

DAPA: 2,3-diaminopropanoic acid, DABA: 2,4-diaminobutanoic acid, ABA: 2-amino-2-butenoic acid, OHVal: 3-hydroxyvaline. L-Configuration was observed for DAPA, Leu, DABA, Thr, Val, OHVal, Asp and Asn, whereas D-configuration was observed for Phe.

Example 2: Synthesis of U747

The synthesis of U747 is made in analogy with the synthesis of the polypeptin PE2, as described by Mountford et al (Org. Biomol. Chem., 2017, 15, 7173-7180). Most amino acids are commercially available in their $N^\alpha$-Fmoc protected form (L-Leu, L-DABA($N^\gamma$-Boc), L-Thr(O-tBu), L-DAPA($N^\beta$-Boc), D-Phe and L-Asp(O-tBu)) whereas unprotected L-OHVal is commercially available and is easily $N^\alpha$-Fmoc and O-tBu protected. The tert-butyl ester of L-allo-Thr is commercially available.

First, a dipeptide is formed by linking Fmoc-L-DABA($N^\gamma$-Boc) to L-allo-Thr(OH) tert-butyl ester, using N-(3-dimethylaminopropyl)-N'-ethylcarbodiimide/triethylamine for the coupling. Then, (E)-ABA is obtained in this dipeptide by dehydration using Martin's sulfurane [Yokokawa and Shioiri, Tetrahedron Letters 43 (2002) 8679-8682] (FIG. 1; in Scheme 1), followed by preparative HPLC to isolate the E-isomer from the predominant Z-isomer. The dipeptide Fmoc-L-DABA($N^\gamma$-Boc)-(E)-DABA is linked to the 2-chlorotrityl resin using collidine in DMF, and the linear peptide Fmoc-L-DAPA(N-Boc)-L-Leu-L-DABA($N^\gamma$-Boc)-(E)-ABA-Resin is synthesized by solid-phase peptide synthesis using 20% piperidine in DMF for Fmoc deprotection of the resin bound peptide before each coupling step and using HCTU (O-(1H-6-chlorobenzotriazole-1-yl)-1,1,3,3-tetramethyluronium hexafluorophosphate)/DIPEA (N,N-diisopropylethylamine) in DMF in each coupling step (FIGS. 1 and 2; in Scheme 1 and 2). The required ester building block (Fmoc-L-Asp(O-tBu)-O—CH[$(CH_2)_6$—$CH_3$]—$CH_2$—COOH) of the depsipeptide is synthesized from Fmoc-L-Asp(O-tBu) and allyl (R/S)-3-hydroxydecanoate, in analogy with the procedure of Mountford et al (Org. Biomol. Chem., 2017, 15, 7173-7180). Following removal of the allyl group using palladium tetrakis triphenylphosphine, the ester building block is linked to the resin bound linear peptide using HCTU/DIPEA in DMF. Subsequently, the linear depsipeptide Fmoc-L-Thr-L-DAPA($N^\beta$-Boc)-D-Phe-L-OHVal-L-Asp(O-tBu)-O—CH[$(CH_2)_6$—$CH_3$]—$CH_2$—CO-L-DAPA($N^\beta$-Boc)-L-Leu-L-DABA($N^\gamma$-Boc)-(E)-ABA-Resin is synthesized as above. After Fmoc deprotection, the N-Boc and O-tBu protected depsipeptide is released from the resin using HFIP (hexafluoroisopropanol) in dichloromethane. Subsequently, the depsipeptide is cyclized by creating a peptide bond between the N-terminal L-Thr and the C-terminal (E)-ABA residues, using PyClocK (6-chlorobenzotriazole-1-yloxy-tris-pyrrolidino-phosphonium hexafluorophosphate)/DIPEA in DMF. Finally, the side chain protecting groups (N-Boc and O-tBu) are removed by treatment with TFA/TIPS (triisopropylsilane) and the peptide U747 is purified from the (S)-3-hydroxydecanoic acid diastereomer by preparative HPLC (column as above, 17.5-35% MeCN in 28 min and 35-57.5% in 7 min, 0.2% formic acid, 10 mL/min).

Example 3: Biological Characterization of U747

Minimal inhibitory concentration (MIC) of U747 against a panel of different pathogenic bacteria was measured by means of two methods A) a broth micro-dilution method in 96-wells microtiter plates and B) according to Clinical and Laboratory Standards Institute (CLSI) guidelines (Clinical and Laboratory Standards Institute (CLSI). 2015. M7-A10. Methods for dilution antimicrobial susceptibility tests for bacteria that grow aerobically, 10th ed. Approved standard. CLSI, Wayne, PA).

A) In the broth micro-dilution method, the test media were either AM3 Broth (BD Difco Ltd) mixed with phosphate buffered saline (PBS, Amresco LLC, Solon, USA) in 1:4 ratio (E. coli, A. baumannii, Enterobacter cloacae, Klebsiella pneumonia and P. aeruginosa), AM3 Broth mixed with PBS in 1:1 ratio (S. aureus) or Malt Extract (ME; 15 g Malt Extract Dico Ltd. in 1000 mL deionized $H_2O$; Aspergillus fumigatus). Prior to MIC-tests, the bacterial cell concentration/fungal spore concentration was adjusted to between 1 and $5×10^5$ cells/spores per mL. Cell concentration was, always, confirmed by viable cell counting done according to standard dilution method and plating the respective bacterial pathogen on VPA-plates (10 g VPB (Oxoid Ltd.), 15 g Bacto Agar (Saveen Werner AB) in 1000 mL deionized $H_2O$) and A. fumigatus on Malt Extract plates (15 g Malt Extract Dico Ltd., 15 g Bacto Agar (Saveen Werner AB) in 1000 mL deionized $H_2O$ directly after each of MIC-tests. Plates were, subsequently, incubated at 37° C. in the dark, and viable colonies counted after 16 to 24 h. In order to estimate MIC (concentration range between 0.05 and 64 μg/mL), the appropriate sample volumes of tested compounds out of the stock solutions of 100, 10 and 1 and if needed 0.1 μg/mL in MeOH were dispensed into the wells of microtiter plate(s) and the solvent was evaporated in a fume-hood. Afterwards, suspensions of pathogen cells in the appropriate medium were dispensed to the wells of microtiter plates and the growth of pathogens were monitored after 16 to 20 h of incubation at 37° C. in the dark. Positive control comprised respective pathogen cells suspended in untreated sterile appropriate media without addition of compounds(s) and negative control comprised the medium only. The MIC was defined as the lowest concentration of each compound with no visible growth of pathogen. All MIC tests were performed in duplicate and/or triplicate and repeated at least twice.

B) Additionally, MIC values for U747 against a selection of pathogens were determined according to Clinical and Laboratory Standards Institute (CLSI) guidelines.

$IC_{50}$, haemolysis rate and frequency of resistance (FoR, Table 4) was determined using standard protocols by different CROs.

Example 4: Alternative Synthesis of U747

First, the required ester building block (EBB, Scheme 3) is synthesised from Fmoc-L-Asp(OtBu)OH (commercial)

and allyl (3R)-3-hydroxydecanoate (synthesised as described below), using DMAP/EDCl as coupling reagents. (3R)-3-Hydroxydecanoic acid is synthesised from (4R,6R)-2-heptyl-4,6-dimethyl-1,3-dioxane (Bartlett, P. A. et al., JACS 1983, 105, 2088-2089) and 1-tert-butoxyvinyloxy-tert-butyl-dimethyl-silane (Wenzel, A. G. and Jacobsen, E. N., JACS 2002, 124, 44, 12964-12965), in a TiCl$_4$-promoted diastereoselective coupling reacting (Elliot, J. D. et al., Tet. Lett 1985, 26, 2535-2538), followed by oxidation using Jones reagent and β-elimination (KOH/MeOH). The allyl (3R)-3-hydroxydecanoate is obtained by reaction with allyl bromide. After coupling with Fmoc-L-Asp(OtBu)OH, the allyl group is removed by PhSiH$_3$/Pd, to yield the EBB for use in subsequent coupling reaction.

Second, (E)-2-azido-2-butenoic acid and the 2-diphenylphosphanylphenyl ester of Fmoc-L-DABA(N$^b$—Boc) are synthesised as shown below (Scheme 3). These components are used in the Staudinger ligation step (Kohn, M. and Breinbauer, R. 2004. ANGEW. CHEMIE-INT. ED. 43 3106-3116) of the solid-phase peptide synthesis. Stereoselective hydrostannation (Miyake, H.; Yamamura, K. Chem. Lett. 1989, 18, 981-984) of ethyl but-3-ynoate (commercial) followed by iodostannation (Hanson, R. N. and El-Wakil, H. J., 1987, Org. Chem., 52, 3687-3688) gives ethyl (E)-2-iodo-2-buteneoate, which is converted to ethyl (E)-2-azido-2-butenoate by treatment with sodium azide and then hydrolysed to (E)-2-azido-2-butenoic acid. Fmoc-L-DABA(N$^δ$-Boc) and 2-diphenylphospanylphenol (commercial) are coupled using DMAP/EDCl to form the corresponding ester. Subsequently, a linear peptide is synthesised (Scheme 4 and 5) starting from Cl-Trityl-resin bound L-Leu, using 1) Fmoc-L-DAPA(N$^δ$-Boc) (commercial), 2) EBB (above), 3) Fmoc-L-3-OH-Val (commercial), 4) Fmoc-D-Phe (commercial), 5) Fmoc-L-DAPA(N$^γ$-Boc), 6) Fmoc-L-Thr(OtBu) (commercial), 7) (E)-2-azido-2-butenoic acid, 8) diphenylphospanylphenyl ester of Fmoc-L-DABA(N-Boc). Couplings 1-5 and 7 are made with PyBOP/HOBt/DIPEA/DMF, coupling 6 with DEBPT/DIPEA/DMF and coupling 8 is made with THF/H$_2$O (Staudinger ligation). Fmoc deprotection is made with 20% piperidine in DMF. The peptide is cleaved from the resin with 20% HFIP in DCM and the peptide is purified by preparative HPLC. Finally, the released peptide is cyclized using PyBOP/HOBt/DIPEA/DMF, and the cyclized peptide is deprotected with TFA/TIPS. Preparative HPLC affords pure U747.

TABLE 3

MIC values (μg/mL) for U747, determined using method A or method B.

| pathogen/test | strain ID | Type/Resistance pattern | MIC | Method |
|---|---|---|---|---|
| A. baumanii | EN007 | WT | 8 | B |
| A. baumanii | EN016 | BM4454 8 | 8 | B |
| A. baumanii | EN017 | BM4652 (efflux-defective) | 8 | B |
| A. baumannii | LMG1041T | WT | 1-2 | A |
| A. baumannii | A219 | CARBA | 1-2 | B |
| A. baumannii | A250 | CARBA | 1-2 | B |
| As. fumigatus | | | 16-32 | A |
| E. cloacae | LMG2783T | WT | 2-4 | A |
| E. coli | LMG15862 | β-lactamase | 2-4 | A |
| E. coli | EC4163 | CARBA | 0.5-1 | B |
| E. coli | EC4129 | CARBA | 1-2 | B |
| E. coli | ATCC25922 | control | 0.5-1 | B |
| E. coli | En001 | WT | 8 | B |
| E. coli | EN002 | DtoIC (efflux-defective) | 8 | B |
| E. coli | EN0137 | ESC, CIP, GEN, SXT | 8 | B |
| E. coli | EN003 | D22 (Ips mutant, hypersensitive) | 4 | B |
| E. coli | EN0134 | ESC, SXT | 4 | B |
| E. coli | EN0135 | ESC (I), GEN, TET | 4 | B |
| E. coli | EN0136 | ESC, GEN, AMK, SXT | 4 | B |
| E. coli | EN0138 | ESC, CIP, SXT, TET, CML | 4 | B |
| E. coli | EN0139 | ESC, CIP, AMK (I), SXT, TET | 4 | B |
| K. pneumoniae | LMG20218 | ESBL | 2-4 | A |
| K. pneumoniae | EN011 | 1161486a (efflux-defective) | 8 | B |
| K. pneumoniae | EN0142 | ESC, ERT, CIP, GEN + TOB, SXT | 8 | B |
| K. pneumoniae | EN006 | WT | 4 | B |
| K. pneumoniae | EN010 | 1161486 | 8 | B |
| K. pneumoniae | EN0140 | ESC, CARBA, CIP, GEN + AMK, SXT, CML | 8 | B |
| K. pneumoniae | EN0141 | ESC, CIP, GEN, SXT, TET, CML | 8 | B |
| K. pneumoniae | EN0143 | ESC, CIP, AMK (I), TOB, SXT | 8 | B |
| K. pneumoniae | EN0144 | ESC, CARBA, CIP, GEN, AMK, SXT, TET | 8 | B |
| P. aeruginosa | LMG6395 | WT | 8-16 | A |
| P. aeruginosa | PS992 | CARBA | 2-4 | B |
| P. aeruginosa | PS826 | CARBA | 2-4 | B |
| P. aeruginosa | ATCC27853 | control | 2-4 | B |
| P. aeruginosa | EN004 | PAO1 WT | 32 | B |
| P. aeruginosa | EN005 | PAO750 (efflux-defective) | 32 | B |
| S. aureus | LMG15975 | MRSA | >32 | A |
| S. aureus | EN008 | ATCC 29213 WT | 64 | B |

WT: wild type; ESC: Extended-spectrum cephalosporin; STX: Trimethoprim-sulfa; GEN: Gentamicin; AMK: Amikacin; CIP: Ciprofloxacin; TET: Tetracycline; CML: Chloramphenicole; CARBA: carbapenem; ESBL: extended spectrum β-lactamase; MRSA: methicillin-resistant Staphylococcus aereus.

TABLE 4

IC$_{50}$ and haemolysis rate and Frequency of Resistance (FoR) for U747, as determined by different CROs.

| Test | Cells/strain ID | comment | |
|---|---|---|---|
| IC$_{50}$ | HepG2 | Human liver cell line | 50 (μg/mL) |
| Haemolysis rate | | 100 μM | 0.6% |
| FOR | E. coli EN001 | @4 × MIC and 8 × MIC | <2 × 10$^{-9}$ |
| FOR | E. coli EN002 | @4 × MIC and 8 × MIC | <2 × 10$^{-9}$ |

MIC values for other compounds (Table 5) of the invention were determined using method A.

TABLE 5

MIC values (μg/mL) and IC$_{50}$ (μg/mL) for selected compounds of the invention. MIC values were determined according to method A and IC$_{50}$ was determined by a CRO using a standard protocol. All MIC values were determined as concentration ranges, and only the lower limits are shown here (i.e. "16" means "16-32" and "1" means "1-2". (nd = not determined).

| | U744 | U747 | U751 | U754 | U755a | U755b | U756 | U757 | U771 | U773 | U775 | U793 | U800 | U810 | U824 | U826 | U842 |
|---|---|---|---|---|---|---|---|---|---|---|---|---|---|---|---|---|---|
| IC$_{50}$ (HepG2) | 72 | 50 | 29 | 20 | 39 | 34 | nd | 28 | 9 | 8 | 9 | 9 | 12 | 15 | 35 | 23 | 22 |
| E. coli LMG15862 | 16 | 2 | 2 | 4 | 8 | 8 | 1 | 8 | 1 | 2 | 4 | 4 | 8 | 8 | 16 | 8 | 16 |
| A. baumannii LMG1041T | 16 | 1 | 4 | 2 | 8 | 2 | 1 | 4 | 1 | 4 | 8 | 4 | 8 | 8 | 16 | 8 | 8 |
| E. cloacae LMG2783T | 16 | 2 | 4 | 4 | 8 | 2 | 2 | 8 | 2 | 8 | 4 | 16 | 8 | 8 | >32 | 16 | >32 |
| K. pneumonia LMG20218 | 8 | 2 | 4 | 4 | 8 | 8 | 2 | 8 | 2 | 16 | 16 | >32 | >32 | >32 | >32 | >32 | >32 |
| P. aeruginosa LMG6395 | 16 | 8 | 8 | 8 | 8 | 4 | 4 | 8 | 2 | 8 | 4 | 8 | 16 | >32 | >32 | 16 | 16 |
| S. aureus LMG15975 | >32 | >32 | 16 | 8 | 16 | 16 | 4 | 16 | 2 | 16 | 16 | >32 | 16 | 16 | >32 | 16 | 8 |

The invention claimed is:
1. An isolated or synthesized compound comprising the formula (I) as presented below:

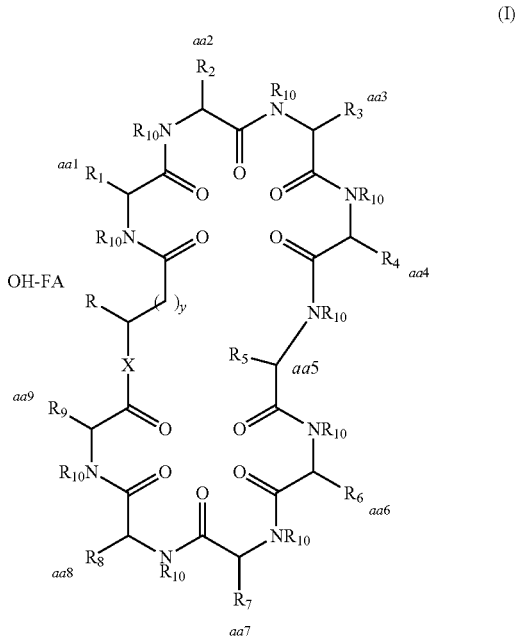

(I)

wherein
y: 1;
X: O;
R: $C_6$-$C_{10}$ n-alkyl or $C_6$-$C_{10}$ n-alkenyl, with 0 or 1 methyl branch;
$R_1$: —$CH_2$—$NH_2$;
$R_2$: —$CH_2$—$CH(CH_3)$—$CH_3$;
$R_3$: —$CH_2$—$CH_2$—$NH_2$;
$R_4$: E or Z=CH—$CH_3$;
$R_5$: —CH(OH)—$CH_3$;
$R_6$: —$CH_2$—$NH_2$;
$R_7$: —$CH_2$-Ph;
$R_8$: $CH(CH_3)$—$CH_3$ or —$COH(CH_3)$—$CH_3$;
$R_9$: —$CH_2$—COOH; and
$R_{10}$: —H
or an enantiomer, diastereomer, tautomer, or pharmaceutically acceptable salt thereof, wherein each stereocenter may be either R or S.
2. A compound according to claim 1, wherein $R_4$: Z=CH—$CH_3$.
3. A compound according to claim 1, wherein the stereocenter of 3-OH FA and each stereocenter of aa1, aa6 and aa7, respectively, may be R or S; and each stereocenter of aa2-aa5, aa8, and aa9 are S, and the stereocenter of $R_5$ is R.
4. The compound according to claim 1, wherein $R_5$: —CHOH—$CH_3$, wherein the stereocenter is R.
5. The compound according to claim 1, wherein $R_8$: —$COH(CH_3)$—$CH_3$ and the stereocenter of the OH-FA is R; each stereocenter of aa1-aa3, aa5, aa6, aa8, and aa9 are S; and the stereocenter of aa7 is R.
6. A composition comprising a compound according to claim 1 in combination with a carrier and/or adjuvant suitable for use in a medicament.
7. The composition according to claim 6, wherein said carrier and/or adjuvant is suitable for use in the treatment of at least one infection caused by one or more Gram-positive or Gram-negative bacteria.
8. The composition according to claim 7, wherein said carrier and/or adjuvant is suitable for use in the treatment of an infection caused by one or more Gram-positive bacteria.
9. The composition according to claim 8, wherein said carrier and/or adjuvant is suitable for use in the treatment of an infection caused by one or more Gram-positive bacteria selected from the group consisting of *Actinomyces; Bacillus; Clostridium; Corynebacterium; Enterococcus; Gardnerella; Lactobacillus; Listeria; Micrococcus; Mycobacteria; Nocardia; Staphylococcus*; and *Streptococcus*.
10. The composition according to claim 7, wherein said carrier and/or adjuvant is suitable for use in the treatment of an infection caused by one or more Gram-negative bacteria.
11. The composition according to claim 10, wherein said carrier and/or adjuvant is suitable for use in the treatment r of an infection caused by one or more Gram-negative bacteria selected from the group consisting of *Acinetobacter; Batronella; Bordetella; Borrelia; Brucella; Burkholderia; Campylobacter; Chlamydia; Chlamydophilia; Citrobacter; Coxiella; Ehrlichia; Enterobacter; Escherichia; Francisella; Fusobacterium; Haemophilus; Helicobacter; Klebsiella; Legionella; Leptospira; Moraxella; Mycoplasma; Neisseria; Proteus; Pseudomonas; Rickettsia; Salmonella; Serratia: Shigella; Treponema; Vibrio*; and *Yersinia*.
12. A method of treating an infection caused by one or more Gram-positive or Gram-negative bacteria, wherein a subject in need thereof is treated with a compound according to claim 1.
13. The method according to claim 12, wherein the infections are caused by one or more Gram-positive bacteria.
14. The method according to claim 13, wherein said one or more Gram-positive bacteria are selected from the group consisting of *Actinomyces; Bacillus; Clostridium; Corynebacterium; Enterococcus; Gardnerella; Lactobacillus; Listeria; Micrococcus; Mycobacteria; Nocardia; Staphylococcus*; and *Streptococcus*.
15. The method according to claim 12, wherein the infections are caused by one or more Gram-negative bacteria.
16. The method according to claim 15, wherein said one or more Gram-negative bacteria are selected from the group consisting of *Acinetobacter; Batronella; Bordetella; Borrelia; Brucella; Burkholderia; Campylobacter; Chlamydia; Chlamydophilia; Citrobacter; Coxiella; Ehrlichia; Enterobacter; Escherichia; Francisella; Fusobacterium; Haemophilus; Helicobacter; Klebsiella; Legionella; Leptospira; Moraxella; Mycoplasma; Neisseria; Proteus; Pseudomonas; Rickettsia; Salmonella; Serratia: Shigella; Treponema; Vibrio*; and *Yersinia*.
17. A pharmaceutical preparation comprising a compound according to claim 1 together with pharmaceutically acceptable carrier(s) and/or adjuvant(s).
18. The pharmaceutical preparation according to claim 17 wherein said pharmaceutically acceptable carrier(s) and/or adjuvant(s) are suitable for use in iv formulations, oral formulations, topical formulations and other formulations giving an optimal effect against the disease causing bacteria, while at the same time giving minimal inhibition of harmless and beneficial bacteria.
19. The preparation according to claim 18, wherein said pharmaceutically acceptable carrier(s) and/or adjuvant(s) are suitable for use in formulations for treating diseases caused by bacteria selected from the group consisting of *Acinetobacter; Bacillus; Campylobacter; Chlamydia: Clostridium; Enterobacter; Enterococcus; Escherichia; Haemophilus; Helicobacter; Klebsiella; Legionella; Myco-* bacteria; *Neisseria*; *Pseudomonas*; *Salmonella*; *Shigella*; *Staphylococcus*; *Streptococcus*; *Vibrio*; and *Yersinia*.

20. The preparation according to claim 18, wherein the disease-causing bacteria are resistant, and/or multiresistant, to antibiotics selected from the group consisting of aminoglycosides; ansamycins; carbapenems; cephalosporins; fluoroquinolons; glycopeptides; lincosamides; lipopeptides; macrolides; monobactams; nitrofurans; oxazolidinones; penicillin; polypeptides; quinolones; sulphonamides; and tetracyclines.

21. A method for decolonization of a surface colonized by Gram-positive and/or Gram-negative bacteria, comprising applying a compound according to claim 1 to said surface.

22. The method according to claim 21, wherein the surface is a body surface.

23. The method according to claim 21, wherein the surface is a part of clinical equipment, such as the surface of a metal or plastic article.

* * * * *